US010551325B2

(12) United States Patent
Koldiaev et al.

(10) Patent No.: US 10,551,325 B2
(45) Date of Patent: Feb. 4, 2020

(54) SYSTEMS FOR PARSING MATERIAL PROPERTIES FROM WITHIN SHG SIGNALS

(71) Applicant: FemtoMetrix, Inc., Santa Ana, CA (US)

(72) Inventors: Viktor Koldiaev, Morgan Hill, CA (US); Marc Christopher Kryger, Fountain Valley, CA (US); John Paul Changala, Tustin, CA (US); Jianing Shi, Sunnyvale, CA (US)

(73) Assignee: FemtoMetrix, Inc., Santa Ana, CA (US)

( * ) Notice: Subject to any disclaimer, the term of this patent is extended or adjusted under 35 U.S.C. 154(b) by 583 days.

(21) Appl. No.: 14/939,750

(22) Filed: Nov. 12, 2015

(65) Prior Publication Data

US 2016/0131594 A1    May 12, 2016

Related U.S. Application Data

(60) Provisional application No. 62/078,636, filed on Nov. 12, 2014.

(51) Int. Cl.
*G01N 21/88* (2006.01)
*G01N 21/95* (2006.01)

(52) U.S. Cl.
CPC .......... *G01N 21/9501* (2013.01); *G01N 2201/06113* (2013.01)

(58) Field of Classification Search
None
See application file for complete search history.

(56) References Cited

U.S. PATENT DOCUMENTS

| 3,850,508 A | 11/1974 | Sittig et al. |
| 4,286,215 A | 8/1981 | Miller |
| 4,291,961 A | 9/1981 | Takayama |
| 5,294,289 A | 3/1994 | Heinz et al. |
| 5,557,409 A | 9/1996 | Downer et al. |

(Continued)

FOREIGN PATENT DOCUMENTS

| EP | 0 710 848 | 5/1996 |
| JP | 2004-226224 | 8/2004 |

(Continued)

OTHER PUBLICATIONS

Tatiana V.Murzina, Optical Second Harmonic Generation in Semiconductor Nanostructures, Mar. 16, 2012, 11 pages.*

(Continued)

*Primary Examiner* — Tung S Lau
(74) *Attorney, Agent, or Firm* — Knobbe, Martens, Olson & Bear, LLP

(57) ABSTRACT

Semiconductor metrology systems based on directing radiation on a wafer, detecting second harmonic generated (SHG) radiation from the wafer and correlating the second harmonic generated (SHG) signal to one or more electrical properties of the wafer are disclosed. The disclosure also includes parsing the SHG signal to remove contribution to the SHG signal from one or more material properties of the sample such as thickness. Systems and methods described herein include machine learning methodologies to automatically classify obtained SHG signal data from the wafer based on an electrical property of the wafer.

8 Claims, 17 Drawing Sheets

(56) References Cited

U.S. PATENT DOCUMENTS

| | | | |
|---|---|---|---|
| 5,814,820 | A | 9/1998 | Dong et al. |
| 6,147,799 | A | 11/2000 | MacDonald |
| 6,321,601 | B1 | 11/2001 | Maris |
| 6,356,377 | B1 | 3/2002 | Bishop et al. |
| 6,650,800 | B2 | 11/2003 | Litvin |
| 6,795,175 | B2 | 2/2004 | Hunt |
| 6,751,374 | B2 | 6/2004 | Wu et al. |
| 6,781,686 | B2 | 8/2004 | Hunt |
| 6,788,405 | B2 | 9/2004 | Hunt |
| 6,791,099 | B2 | 9/2004 | Some et al. |
| 6,819,844 | B2 | 11/2004 | Hunt |
| 6,856,159 | B1* | 2/2005 | Tolk ............ G01R 31/311 324/754.23 |
| 6,882,414 | B2 | 4/2005 | Hunt |
| 6,900,894 | B2 | 5/2005 | McMillen et al. |
| 7,158,284 | B2 | 1/2007 | Alles et al. |
| 7,259,868 | B2 | 8/2007 | Ozcan et al. |
| 7,304,305 | B2 | 12/2007 | Hunt |
| 7,324,267 | B2 | 1/2008 | Melloni et al. |
| 7,355,618 | B2 | 4/2008 | Seto et al. |
| 7,433,056 | B1* | 10/2008 | Janik ............ G01B 11/0616 356/301 |
| 7,580,138 | B2 | 8/2009 | Price |
| 7,592,828 | B2 | 9/2009 | Song |
| 7,595,204 | B2 | 9/2009 | Price |
| 7,616,307 | B2 | 11/2009 | Murtagh et al. |
| 7,659,979 | B2 | 2/2010 | Murtagh et al. |
| 7,684,047 | B2 | 3/2010 | Drake et al. |
| 7,718,969 | B2 | 5/2010 | Zhang et al. |
| 7,781,739 | B1 | 8/2010 | Jannson et al. |
| 8,049,304 | B2 | 11/2011 | Srividya et al. |
| 8,143,660 | B2 | 3/2012 | Lee et al. |
| 8,525,287 | B2 | 9/2013 | Tian et al. |
| 8,573,785 | B2 | 11/2013 | Kuksenkov et al. |
| 8,755,044 | B2 | 6/2014 | Reich et al. |
| 9,018,968 | B2 | 4/2015 | Huang et al. |
| 9,194,908 | B2 | 11/2015 | Heidmann |
| 9,285,338 | B2 | 3/2016 | Dickerson et al. |
| 9,652,729 | B2* | 5/2017 | Hoffman, Jr. .... G06Q 10/06395 |
| 9,759,656 | B2 | 9/2017 | Ito et al. |
| 2003/0031443 | A1* | 2/2003 | Soljacic .......... B29D 11/00721 385/125 |
| 2003/0148391 | A1 | 8/2003 | Salafsky |
| 2005/0024476 | A1* | 2/2005 | Seto ............ B41J 2/473 347/239 |
| 2005/0058165 | A1 | 3/2005 | Morehead et al. |
| 2006/0044641 | A1* | 3/2006 | Alles ............ G01N 21/63 359/328 |
| 2008/0285606 | A1* | 11/2008 | Kippenberg ............ G02F 1/39 372/32 |
| 2009/0051926 | A1* | 2/2009 | Chen ............ G01B 11/022 356/511 |
| 2010/0208757 | A1 | 8/2010 | Hu |
| 2010/0272134 | A1* | 10/2010 | Blanding ............ G02F 1/377 372/22 |
| 2011/0125458 | A1 | 5/2011 | Xu et al. |
| 2012/0127437 | A1* | 5/2012 | Kuksenkov ............ G03B 21/40 353/31 |
| 2013/0110448 | A1* | 5/2013 | Hoffman, Jr. .... G06Q 10/06395 702/127 |
| 2015/0330908 | A1 | 11/2015 | Koldiaev et al. |
| 2015/0330909 | A1 | 11/2015 | Koldiaev et al. |
| 2015/0331029 | A1 | 11/2015 | Koldiaev et al. |
| 2015/0331036 | A1* | 11/2015 | Koldiaev ............ G01N 21/8806 324/754.23 |
| 2016/0131594 | A1* | 5/2016 | Koldiaev ............ G01N 21/9501 702/40 |
| 2017/0067830 | A1 | 3/2017 | Adell et al. |
| 2018/0217192 | A1 | 8/2018 | Koldiaev et al. |
| 2018/0217193 | A1 | 8/2018 | Koldiaev et al. |
| 2018/0292441 | A1 | 10/2018 | Koldiaev et al. |
| 2018/0299497 | A1 | 10/2018 | Koldiaev et al. |

FOREIGN PATENT DOCUMENTS

| | | |
|---|---|---|
| TW | 200421460 | 10/2004 |
| WO | WO 00/55885 | 9/2000 |
| WO | WO 2015/161136 | 10/2015 |
| WO | WO 2016/077617 | 5/2016 |
| WO | WO 2017/041049 | 3/2017 |

OTHER PUBLICATIONS

Tatiana V.Murzina, Optical Second Harmonic Generation in Semiconductor Nanostructures, 2012, 11 pages. (Year: 2012).*

Paul Campagnola, Second Harmonic Generation Imaging Microscopy: Applications to Diseases Diagnostics, Anal Chem. May 1, 2011; 83(9): 3224-3231 (Year: 2011).*

Stefano Marano, Sequential Detection of Almost-Harmonic Signals, IEEE Transactions on Signal Processing, vol. 51, No. 2, Feb. 2003, 12 pages (Year: 2003).*

"Rapid Non-destructive Characterization of Trap Densities and Layer Thicknesses in HfO2 Gate Materials Using Optical Second Harmonic Generation", Semicon Korea, Santa Ana, California, Jan. 2016, in 24 pages.

Adell, P. C. et al., "Impact of Hydrogen Contamination on the Total Dose Response of Linear Bipolar Micocircuits", IEEE, Aug. 2007, in 8 pages.

Alles, M. et al, "Second Harmonic Generation for Noninvasive Metrology of Silicon-on-Insulators Wafers", IEEE Transactions on Semiconductor Manufacturing, vol. 20(2), May 2007, pp. 107-113, in 7 pages.

An, Y. et al., "Role of photo-assisted tunneling in time-dependent second-harmonic generation from Si surfaces with ultrathin oxides", Applied Physics Letters, vol. 102, Feb. 4, 2013, pp. 051602-051602-4, in 5 pages.

Bierwagen, O. et al., "Dissipation-factor-based criterion for the validity of carrier-type identification by capacitance-voltage measurements", Applied Physics Letters, vol. 94, Apr. 2009, pp. 152110-152110-3, in 3 pages.

Bloch, J. et al., "Electron Photoinjection from Silicon to Ultrathin SiO2 Films via Ambient Oxygen", Physical Review Letters vol. 77(5), Jul. 29, 1996, pp. 920-923, in 4 pages.

Chang, C. L. et al., "Direct determination of flat-band voltage for metal/high κ oxide/semiconductor heterointerfaces by electric-field-induced second-harmonic generation", Applied Physics Letters vol. 98, Apr. 2011, pp. 171902-171902-3, in 3 pages.

Dautrich, M. et al., "Noninvasive nature of corona charging on thermal Si/SiO2 structures", Applied Physics Letters, vol. 85(10), Sep. 6, 2004, pp. 1844-1845, in 2 pages.

De Vries, J. et al., "Measuring the concentration and energy distribution of interface states using a non-contact corona oxide semicondcutor method", Applied Physics Letters, vol. 100, Feb. 24, 2012, pp. 082111-082111-3, in 3 pages.

Dixit, S. K. et al., "Radiation Induced Charge Trapping in Ultrathin HfO2-Based MOSFETs", IEEE Transactions on Nuclear Science, vol. 54(6), Dec. 2007, pp. 1883-1890, in 8 pages.

Erley, G. et al., "Silicon interband transitions observed at Si(100)-SiO2 interfaces", Physical Review B, vol. 58(4), Jul. 15, 1998, pp. R1734-R1737, in 4 pages.

Esqueda, I. et al., "Modeling the Effects of Hydrogen on the Mechanisms of Dose Rate Sensitivity", RADECS 2011 Proceedings—A-1, Sep. 2011, pp. 1-6, in 6 pages.

Fomenko, V. et al., "Optical second harmonic generation studies of ultrathin high-k dielectric stacks", Journal of Applied Physics, American Institute of Physics, vol. 97(8), Apr. 11, 2005, in 8 pages.

Fomenko, V. et al., "Second harmonic generation investigations of charge transfer at chemically-modified semiconductor interfaces", Journal of Applied Physics, vol. 91(7), Apr. 1, 2002, pp. 4394-4398, in 5 pages.

Geiger, F., "Second Harmonic Generation, Sum Frequency Generation and X(3): Dissecting Environmental Interfaces with a Nonlinear Optical Swiss Army Knife", Annual Review of Physical Chemistry, vol. 60(1), Nov. 2008, pp. 61-83, in 25 pages.

(56) References Cited

OTHER PUBLICATIONS

Gielis, J. J. H. et al., "Negative charge and charging dynamics in Al2O3 films on Si characterized by second-harmonic generation", Journal of Applied Physics, American Institute of Physics, vol. 104(7), Nov. 2008, pp. 073701-073701-5, in 6 pages.

Gielis, J. J. H. et al., "Optical second-harmonic generation in thin film systems", Journal of Vacuum Science Technology A, vol. 26(6), Nov./Dec. 2008, pp. 1519-1537, in 20 pages.

Glinka, Y. D. et al., "Ultrafast dynamics of interfacial electric fields in semiconductor heterostructures monitored by pump-probe second-harmonic generation", Applied Physics Letter, vol. 81(20), Nov. 11, 2002, pp. 3717-3719, in 3 pages.

Heinz, T. F. et al., "Optical Second-Harmonic Generation from Semiconductor Surfaces", Advances in Laser Science III, edited by A. C. Tam, J. L. Cole and W. C. Stwalley (American Institute of Physics, New York, 1988) p. 452, in 8 pages.

Istratov, A. et al., "Exponential analysis in physical phenomena", Review of Scientific Instruments, vol. 70(2), Feb. 1999, pp. 1233-1257, in 25 pages.

Jiang, Y. et al., "Finite difference method for analyzing band structure in semiconductor heterostructures without spurious solutions", Journal of Applied Physics, vol. 116(17), Nov. 2014, pp. 173702-173702-9, in 10 pages.

Jozwikowska, A., "Numerical solution of the nonlinear Poisson equation for semiconductor devices by application of a diffusion-equation finite difference scheme", Journal of Applied Physics, vol. 104, Oct. 2008, pp. 063715-1 to 063715-9, in 10 pages.

Jun, H. et al., "Charge Trapping in Irradiated SOI Wafers Measured by Second Harmonic Generation", IEEE Transactions on Nuclear Science, vol. 51(6), Dec. 2004, pp. 3231-3237, in 8 pages.

Kang, A. Y. et al., "The Radiation Response of the High Dielectric-Constant Hafnium Oxid/Silicon System", IEEE Transactions on Nuclear Science, vol. 49(6), Dec. 2002, pp. 2636-2642, in 7 pages.

Katsube, T. et al., "Memory Traps in MNOS Diodes Measured by Thermally Stimulated Current", Solid State Electronics, vol. 19(1), Jan. 1976, pp. 11-16, in 6 pages.

Koldyaev, V. et al., "Rapid Non-Destructive Detection of Sub-Surface Cu in Silicon-On-Insulator Wafers by Optical Second Harmonic Generation", ASMC, May 2015, in 4 pages.

Lantz, J. et al., "Time-Resolved Optical Second Harmonic Generation Measurements of Picosecond Band Flattening Processes at Single Crystal TiO2 Electrodes", The Journal of Physical Chemistry, vol. 98(38), Sep. 1994, pp. 9387-9390, in 4 pages.

Lei, M. et al., "Hot carrier injection from nanometer-thick silicon-on-insulator films measured by optical second harmonic generation", Applied Physics Letters, vol. 96, Jul. 2010, pp. 241105-241105-3, in 3 pages.

Lundstrom, I. et al., "Tunneling to traps in insulators", Journal of Applied Physics, vol. 43(12), Dec. 1972, pp. 5045-5047, in 4 pages.

Lupke, G. et al., "Electron Trapping in Ultrathin SiO2 on Si(001) Probed by Electric-Field-Induced Second-Harmonic Generation", MC22, IEEE Nonlinear Optics: Materials, Fundamentals and Applications—Conference Proceedings, Aug. 1998, pp. 89-91, in 3 pages.

Mandoc, M. M. et al., "Corona Charging and Optical Second-Harmonic Generation Studies of the Field-Effect Passivation of c-Si by Al2O3 Films", IEEE, Jul. 2010, in 5 pages.

Marka, Z. et al., "Band offsets measured by internal photo-emission-induced second-harmonic generation", Physical Review B, vol. 67(4), Jan. 2003, pp. 045302-045302-5, in 6 pages.

Marka, Z. et al., "Band offsets measurement of Si-SiO2 interfaces by internal photoemission induced second-harmonic generation", Physical Review Journal, paper QTuM6, 2003, in 2 pages.

Marka, Z. et al., "Characterization of X-Ray Radiation Damage in Si/SiO2 Structures Using Second-Harmonic Generation", IEEE Transactions on Nuclear Science, vol. 47(6), Dec. 2000, pp. 2256-2261, in 6 pages.

Marka, Z. et al., "Two-color optical technique for characterization of x-ray radiation-enhanced electron transport in SiO2", Journal of Applied Physics, vol. 93(4), Feb. 15, 2003, pp. 1865-1870, in 6 pages.

Mihaychuk, J. G. et al, "Time-dependent second-harmonic generation from the Si-SiO2 interface induced by charge transfer", Optics Letters, vol. 20(20), Oct. 1995, pp. 2063-2065, in 4 pages.

Nagel, J. et al., "Solving the Generalized Poisson Equation Using the Finite-Difference Method (FDM)", Feb. 15, 2012, pp. 1-18, in 18 pages.

Neethling, P. H. et al., "Second harmonic generation as a technique to probe buried interfaces", South African Journal of Science, vol. 105, Jul./Aug. 2009, pp. 282-284, in 3 pages.

Park, H. et al., "Total Ionizing Dose Effects on Strained HfO2-Based nMOSFETs", IEEE Transactions on Nuclear Science, vol. 55(6), Dec. 2008, pp. 2981-2985, in 5 pages.

Pasternak, R. et al., "Laser detection of radiation enhanced electron transport in ultra-thin oxides", Nuclear Instruments and Methods in Physics Research A, vol. 514, 2003, pp. 150-155, in 6 pages.

Pedersen, K. et al., "Spectroscopic second-harmonic generation from silicon-on-insulator wafers", Optical Society of America, vol. 26(5), May 2009, pp. 917-922, in 6 pages.

Powell, R. D., "The Use of Photoinjection to Determine Oxide Charge Distributions and Interface Properties in MOS Structures", IEEE Transactions on Nuclear Sciences, vol. 17(6), Jan. 1971, pp. 41-46, in 6 pages.

Price, J. et al., "Charge trapping defects in Si/SiO2/Hf(1-x)SixO2 film stacks characterized by spectroscopic second-harmonic generation", Journal of Vacuum Science and Technology: Part B, AVS/SIP, vol. 29(4), Jul. 2011, pp. 4D101-4D101-11, in 12 pages.

Price, J. et al., "Optical second-harmonic generation study of charge trapping dynamics in HfO2/SiO2 films on Si(100)", Physica Status Solidi, vol. 5(8), Jun. 2008, pp. 2667-2670, in 4 pages.

Rai, V. N. et al., "A transistorized Marx bank circuit providing sub-nanosecond high-voltage pulses", Measurement Science and Technology, vol. 5(4), Nov. 1993, pp. 447-449, in 3 pages.

Reber, R. et al., "Thermally stimulated current measurements of SiO2 defect density and energy in irradiated metal-oxide-semiconductor capacitors", Review of Scientific Instruments, vol. 63(12), Jun. 4, 1998, pp. 5714-5725, in 13 pages.

Robertson, J., "Band offsets of wide-band-gap oxides and implications for future electronic devices", Journal of Vacuum Science and Technology B, vol. 18(3), May 2000, pp. 1785-1791, in 7 pages.

Schaller, R. D. et al., "Time-Resolved Second Harmonic Generation Near-Field Scanning Optical Microscopy", Chemphyschem, vol. 4(11), Nov. 14, 2003, pp. 1243-1247, in 5 pages.

Shaver, J. et al., "A 2D Finite Difference Simulation to Investigate the High Voltage Blocking Characteristics of 4H-SiC Photoconductive Semiconductor Switches", IEEE, 978-1-4799-8403-9/15, May 2015, pp. 193-195, in 3 pages.

Taguchi, D. et al., "Probing of carrier behavior in organic electroluminescent diode using electric field induced optical second-harmonic generation measurement", Applied Physics Letters, vol. 95, Dec. 30, 2009, pp. 263310-263310-3, in 4 pages.

Ushiki, T. et al., "Evidence of Energetically-Localized Trap-States at SOI-BOX Interface in High-Dose SIMOX Wafers", IEEE International SOI Conference, Oct. 1999, pp. 48-49, in 2 pages.

Vanbel, M. K. et al., "Electric-Field-Induced Second-Harmonic Generation Demonstrates Different Interface Properties of Molecular Beam Epitaxy Grown MgO on Si", The Journal of Physical Chemistry, vol. 118(4), Jan. 2014, in 6 pages.

Vanbel, M. K. et al., "Tunneling of holes is observed by second-harmonic generation", Applied Physics Letters, vol. 102(8), Feb. 2013, in 5 pages.

Vasudevan, V. et al., "A numerical simulation of hole and electron trapping due to radiation in silicon dioxide", Journal of Applied Physics, vol. 70, Nov. 1991, pp. 4490-4495, in 7 pages.

Wang, H. et al., "Non-degenerate fs pump-probe study on InGaN with multi-wavelength second-harmonic generation", Optics Express, Jul. 11, 2005, vol. 13(14), pp. 5245-5252, in 8 pages.

Wang, W. et al., "Coupled Electron-Hole Dynamics at the Si/SiO2 Interface", Physical Review Letters, vol. 81(19), Nov. 9, 1998, pp. 4224-4227, in 4 pages.

White, Y. V. et al., "Studies of charge carrier trapping and recombination processes in Si SiO2 MgO structures using second-harmonic generation", Applied Physics Letters, vol. 88, Feb. 2006, pp. 062102-062102-3, in 3 pages.

(56) References Cited

OTHER PUBLICATIONS

Xiao, D. et al., "Optical probing of a silicon integrated circuit using electric-field-induced second-harmonic generation", Applied Physics Letters, vol. 88, Mar. 17, 2006, pp. 114107-114107-3, in 4 pages.
European Extended Search Report dated Feb. 26, 2019 in corresponding EP Application No. 16843152.6.
European Extended Search Report dated Sep. 28, 2017 in corresponding EP Application No. 15779557.6.
European Extended Search Report dated Apr. 3, 2018 in corresponding EP Application No. 15858539.8.
International Search Report and Written Opinion dated Dec. 21, 2016 in corresponding PCT Application No. PCT/US2016/050286.
International Preliminary Report on Patentability and Written Opinion dated Mar. 6, 2018 in corresponding PCT Application No. PCT/US2016/050286.
Invitation to Pay Addition Fees and Partial Search Report dated Jul. 27, 2015 in corresponding PCT Application No. PCT/US2015/026263.
International Search Report and Written Opinion dated Sep. 23, 2015 in corresponding PCT Application No. PCT/US2015/026263.
International Preliminary Report on Patentability and Written Opinion dated Oct. 27, 2016 in corresponding PCT Application No. PCT/US2015/026263.
International Search Report and Written Option dated Feb. 26, 2016 in corresponding PCT Application No. PCT/US2015/060437.
International Preliminary Report on Patentability and Written Opinion dated May 26, 2017 in corresponding PCT Application No. PCT/US2015/060437.
Taiwanese Office Action dated Sep. 28, 2017 in corresponding TW Application No. 105131588.
U.S. S Office Action dated Jul. 13, 2018 in corresponding U.S. Appl. No. 15/256,442.
U.S. Office Action dated Apr. 4, 2019 in corresponding U.S. Appl. No. 15/256,442.
U.S. Office Action dated Jul. 26, 2019 in corresponding U.S. Appl. No. 15/256,442.
U.S. Office Action dated Feb. 8, 2017 in corresponding U.S. Appl. No. 14/690,179.
U.S. Office Action dated Aug. 28, 2017 in corresponding U.S. Appl. No. 14/690,179.
U.S. Office Action dated Jan. 14, 2019 in corresponding U.S. Appl. No. 15/882,433.
U.S. Office Action dated Jul. 25, 2019 in corresponding U.S. Appl. No. 15/882,433.
U.S. Office Action dated Oct. 13, 2016 in corresponding U.S. Appl. No. 14/690,256.
U.S. Office Action dated Jul. 28, 2017 in corresponding U.S. Appl. No. 14/690,256.
U.S. Office Action dated Oct. 31, 2018 in corresponding U.S. Appl. No. 15/880,308.
U.S. Office Action dated May 1, 2017 in corresponding U.S. Appl. No. 14/690,251.
U.S. Office Action dated Jun. 25, 2018 in corresponding U.S. Appl. No. 15/799,594.
U.S. Office Action dated Apr. 17, 2019 in corresponding U.S. Appl. No. 15/799,594.
U.S. Office Action dated Oct. 7, 2016 in corresponding U.S. Appl. No. 14/690,279.
U.S. Office Action dated May 8, 2017 in corresponding U.S. Appl. No. 14/690,279.
U.S. Office Action dated Sep. 18, 2018 in corresponding U.S. Appl. No. 15/806,271.
U.S. Office Action dated Mar. 29, 2019 in corresponding U.S. Appl. No. 15/806,271.

* cited by examiner

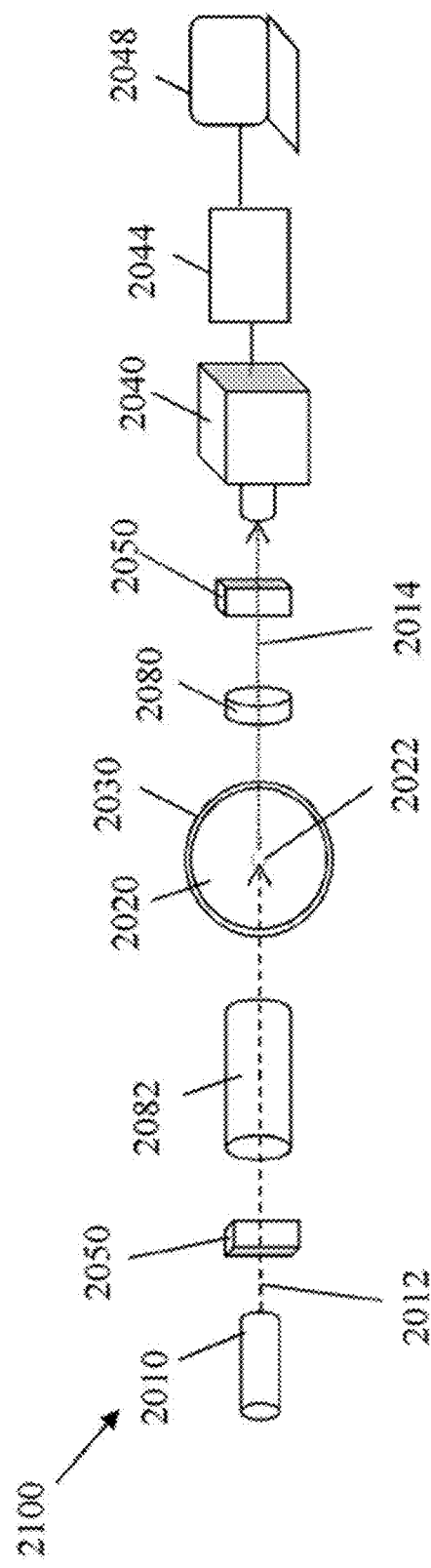

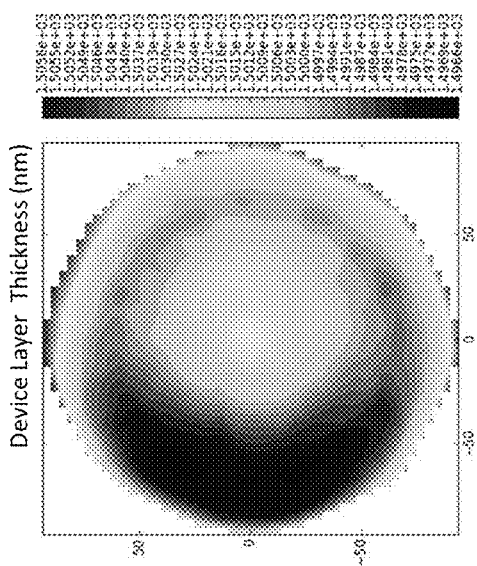
Fig. 4A
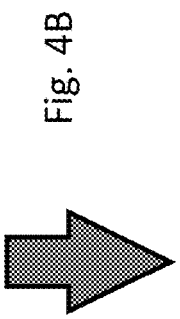
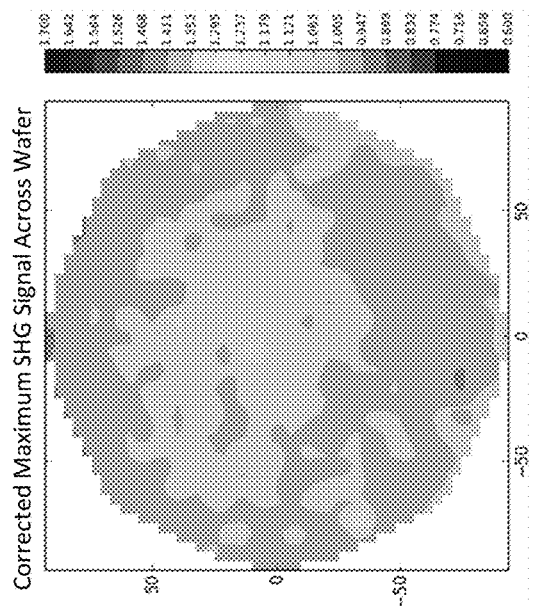
Fig. 4B
Fig. 4C

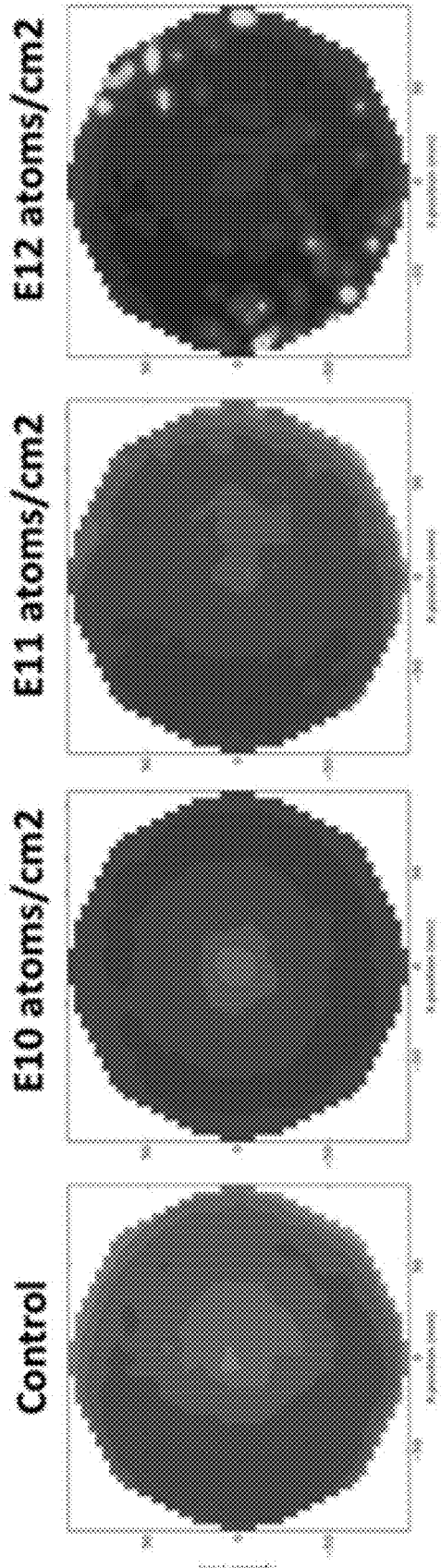
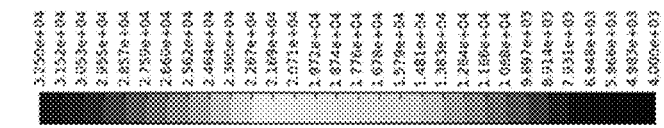
Fig. 6A  Fig. 6B  Fig. 6C  Fig. 6D

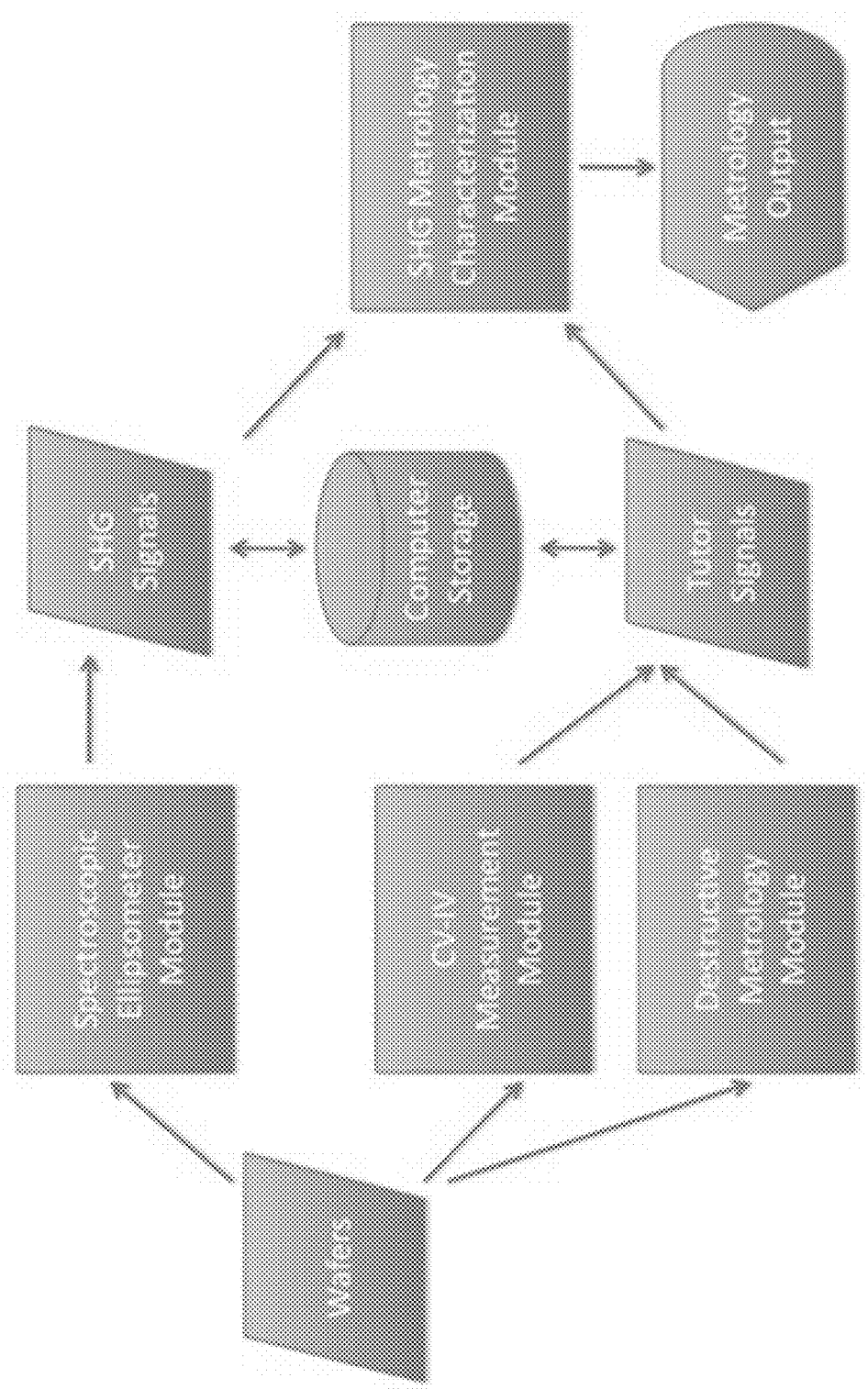
Fig. 8: system architecture

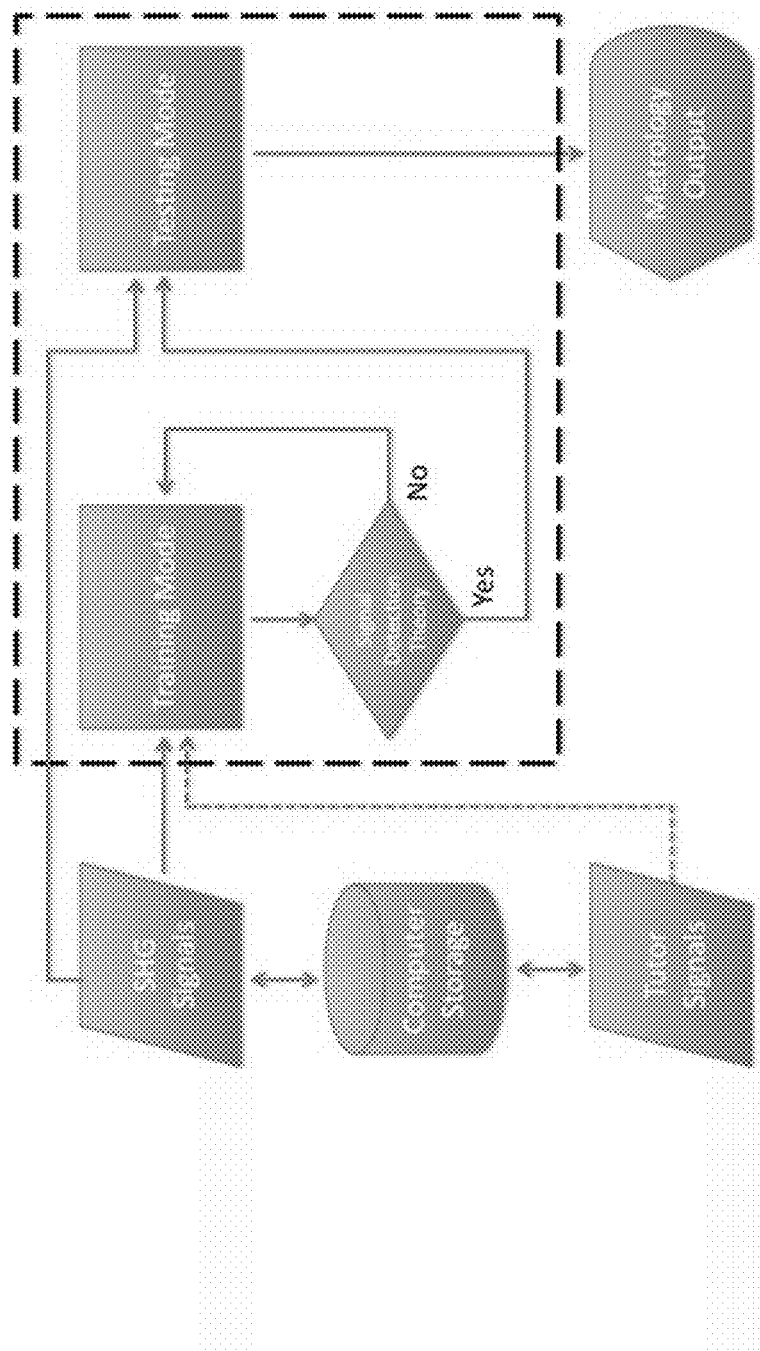
Fig. 10: SHG Characterization Module

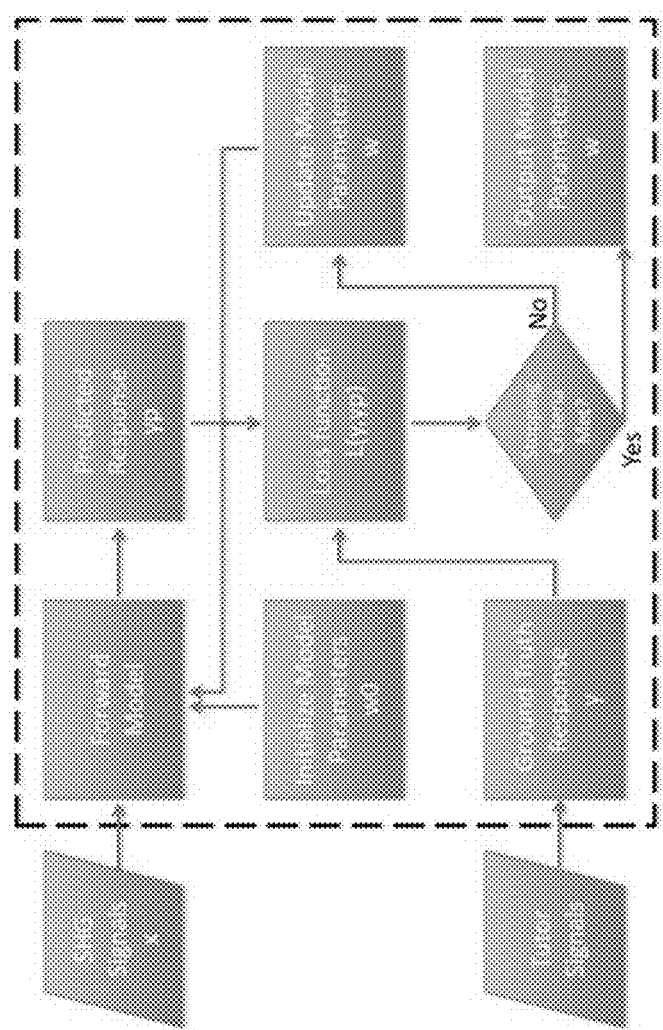
Fig. 11: Supervised Training Mode
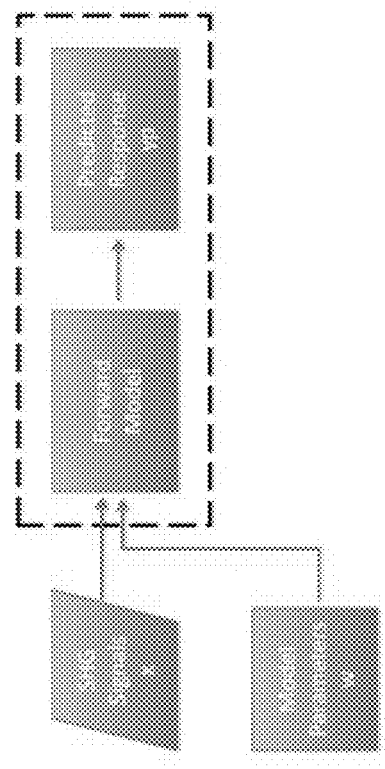
Fig. 12: Supervised Testing Mode

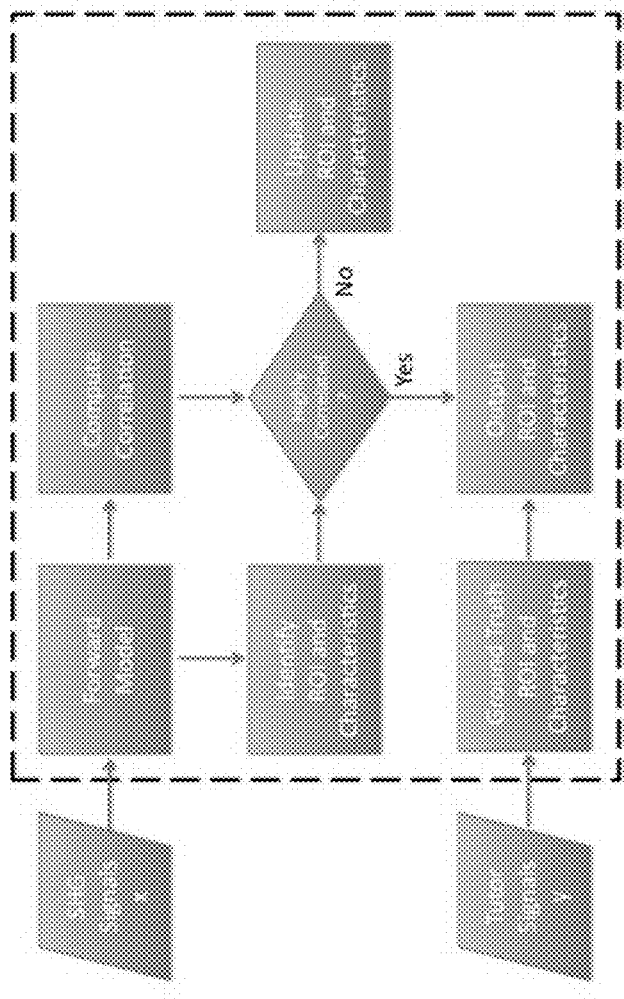
Fig. 13: Unsupervised Training Mode
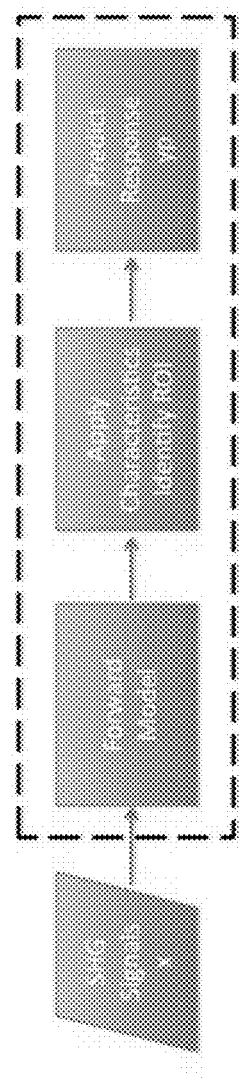
Fig. 14: Unsupervised Testing Mode

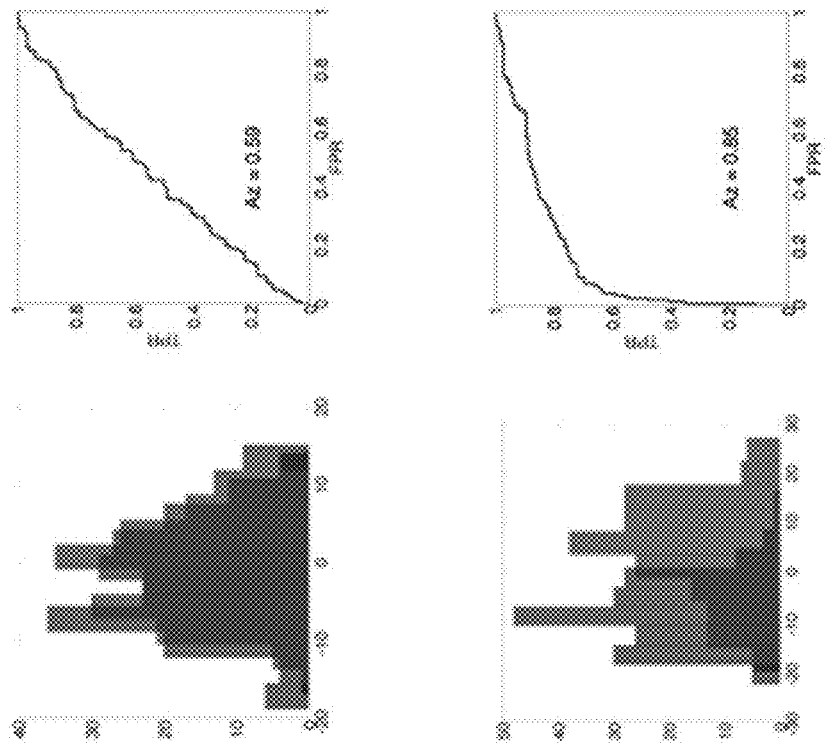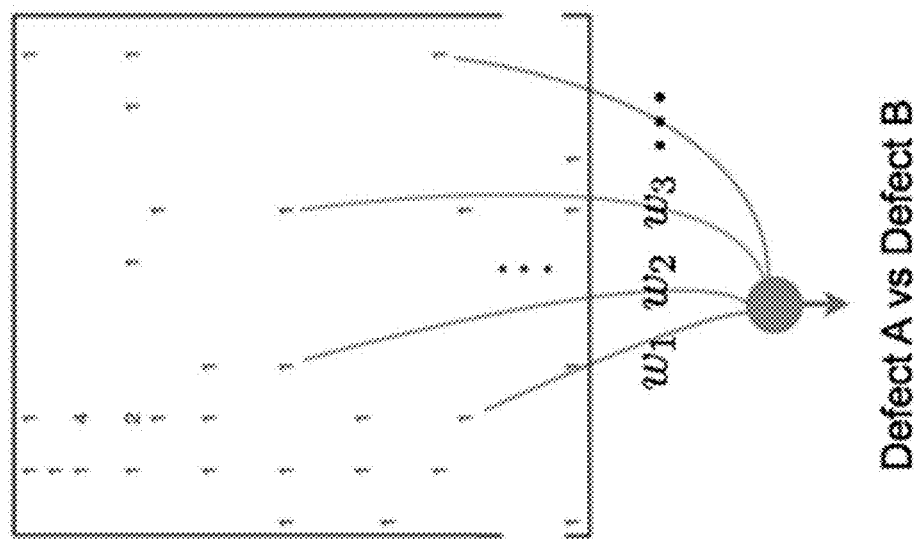
Fig. 17

SYSTEMS FOR PARSING MATERIAL PROPERTIES FROM WITHIN SHG SIGNALS

CROSS-REFERENCE TO RELATED APPLICATIONS

This application claims benefit under 35 U.S.C. § 119(e) of U.S. Provisional Application No. 62/078,636, filed on Nov. 12, 2014, titled "Systems for Parsing Material Properties from Within SHG Signals," which is incorporated by reference herein in its entirety, including but not limited to each of the Sections I, II, III, and IV, of the APPENDIX which are each incorporated herein by reference in their entirety.

FIELD

The subject filing relates to systems for wafer inspection, semiconductor metrology, materials characterization, surface characterization and/or interface analysis.

BACKGROUND

In nonlinear optics, light beam input(s) are output as the sum, difference or harmonic frequencies of the input(s). Second Harmonic Generation (SHG) is a non-linear effect in which light is emitted from a material at a reflected angle with twice the frequency of an incident source light beam. The process may be considered as the combining of two photons of energy E to produce a single photon of energy 2E (i.e., the production of light of twice the frequency (2ω) or half the wavelength) of the incident radiation. The effect can also be generalized as the combining of photons of different energies, corresponding to different frequencies.

Without subscribing to any particular theory, the SHG process does not occur within the bulk of materials exhibiting a center of symmetry (i.e., in inversion or centrosymmetric materials). For these materials, the SHG process is appreciable only at surfaces and/or interfaces where the inversion symmetry of the bulk material is broken. As such, the SHG process offers a unique sensitivity to surface and interface properties.

So-understood, the SHG effect can be useful in detecting interface properties during wafer fabrication in Chemical Vapor Deposition (CVD) processing. Accordingly, SHG techniques can provide a unique non-contact wafer/substrate inspection opportunity.

SUMMARY

The systems employ multiple characterization techniques in one device. Namely, an SHG metrology characterization module is integrated with at least one secondary analysis device including but not limited to: a spectroscopic ellipsometer (SE), a reflectometer, a CV-IV parametric analyzer, an Inductively Coupled Plasma Mass Spectrometry (ICPMS), Vapor Phase decomposition (VPD)-ICPMS, a Total Reflection X-Ray Fluorescence (TXRF), a Secondary Ion Mass Spectrometry (SIMS), a Rutherford Backscattering (RBS), a Scanning/Tunneling Electron Microscope (SEM/TEM), an Atomic Force Microscope (AFM), a Brightfield/Darkfield Microscopy, a Glow Discharge Optical Emission Spectroscopy (GD-OES), an X-Ray Photoelectron Spectroscopy (XPS), a Fourier Transform Infrared Spectroscopy (FTIR), or a microwave detected photoconductive decay (µ-PCD).

One innovative aspect of the subject matter of this disclosure is embodied in a method for characterizing a sample. The method comprises directing a beam of electro-magnetic radiation to a sample using an optical source; detecting a Second Harmonic Generation (SHG) signal using an optical detector, wherein the detected SHG signal includes a portion attributed to one or more material properties of the sample; measuring the one or more material properties of the sample using a secondary analysis device; and under control of an electronic processing circuit: correlating the detected SHG signal with the measured one or more material properties of the sample; removing the portion attributed to one or more material properties of the sample to obtain a parsed SHG signal data; and estimating a characteristic of the sample from the parsed SHG signal data.

In various embodiments, the optical source can be a laser. In various embodiments, the secondary analysis device system can comprise at least one of: a reflectometer, a spectroscopic ellipsometer (SE), a CV-IV parametric analyzer, an Inductively Coupled Plasma Mass Spectrometry (ICPMS), Vapor Phase decomposition (VPD)-ICPMS, a Total Reflection X-Ray Fluorescence (TXRF), a Secondary Ion Mass Spectrometry (SIMS), a Rutherford Backscattering (RBS), a Scanning/Tunneling Electron Microscope (SEM/TEM), Atomic Force Microscope (AFM), Brightfield/Darkfield Microscopy, Glow Discharge Optical Emission Spectroscopy (GD-OES), X-Ray Photoelectron Spectroscopy (XPS), Fourier Transform Infrared Spectroscopy (FTIR), or a microwave detected photoconductive decay (µ-PCD). The one or more material properties of the sample can include at least one of: thickness of one or more layers of the sample or presence of a known artifact. The characteristic of the sample estimated from the parsed SHG signal data can include one or more electrical properties of the sample. The one or more electrical properties of the sample can include at least one of: local surface and subsurface metal; organic or inorganic contaminants; trap charge density; strain or doping levels. In various embodiments, removing the portion attributed to one or more material properties of the sample can comprise determining a quantitative relationship between the measured one or more material properties of the sample and the detected SHG signal; and adjusting the detected SHG signal by an amount of SHG signal that is expected from a sample having the measured one or more material properties. In various embodiments, adjusting the detected SHG signal can comprise dividing the detected SHG signal by an amount of SHG signal that is expected from a sample having the measured one or more material properties. In various embodiments, removing the portion attributed to one or more material properties of the sample can comprise determining a quantitative relationship between the measured one or more material properties of the sample and the detected SHG signal; and deconvoluting the detected SHG signal by an amount of SHG signal that is expected from a sample having the measured one or more material properties.

Another innovative aspect of the subject matter of this disclosure is embodied in a system for characterizing a sample. The system comprises an optical source configured to direct a beam of electro-magnetic radiation to a sample; an optical detector configured to detect a Second Harmonic Generation (SHG) signal, wherein the detected SHG signal includes a portion attributed to one or more material properties of the sample; a secondary analysis device configured to measure one or more material properties of the sample; and an electronic processing circuit. The electronic processing circuit is configured to: correlate the detected SHG signal with the measured one or more material properties of the sample; remove the portion attributed to one or more material properties of the sample to obtain a parsed SHG signal data; and estimate a characteristic of the sample from the parsed SHG signal data.

In various embodiments, the secondary analysis device system can comprise at least one of: a reflectometer, a spectroscopic ellipsometer (SE), a CV-IV parametric analyzer, an Inductively Coupled Plasma Mass Spectrometry (ICPMS), Vapor Phase decomposition (VPD)-ICPMS, a Total Reflection X-Ray Fluorescence (TXRF), a Secondary Ion Mass Spectrometry (SIMS), a Rutherford Backscattering (RBS), a Scanning/Tunneling Electron Microscope (SEM/TEM), Atomic Force Microscope (AFM), Brightfield/Darkfield Microscopy, Glow Discharge Optical Emission Spectroscopy (GD-OES), X-Ray Photoelectron Spectroscopy (XPS), Fourier Transform Infrared Spectroscopy (FTIR), or a microwave detected photoconductive decay (μ-PCD).

In various embodiments, the one or more material properties of the sample includes at least one of: thickness of one or more layers of the sample or presence of a known artifact. In various embodiments, the characteristic of the sample estimated from the parsed SHG signal data can include one or more electrical properties of the sample. The one or more electrical properties of the sample can include at least one of: local surface and subsurface metal; organic or inorganic contaminants; trap charge density; strain or doping levels. In various embodiments, the electronic processing circuit can be configured to remove the portion attributed to one or more material properties of the sample by: determining a quantitative relationship between the measured one or more material properties of the sample and the detected SHG signal; and adjusting the detected SHG signal by an amount of SHG signal that is expected from a sample having the measured one or more material properties.

In various embodiments, adjusting the detected SHG signal can include dividing the detected SHG signal by an amount of SHG signal that is expected from a sample having the measured one or more material properties. In various embodiments, the electronic processing circuit can be configured to remove the portion attributed to one or more material properties of the sample by: determining a quantitative relationship between the measured one or more material properties of the sample and the detected SHG signal; and deconvoluting the detected SHG signal by an amount of SHG signal that is expected from a sample having the measured one or more material properties.

Another innovative aspect of the subject matter of this disclosure is embodied in an automated method of characterizing electrical properties of a sample. The method comprising: receiving a signal from a sample, the signal comprising Second Harmonic Generation (SHG) signal; and under the control of a hardware computing device: processing the received signal to extract features from the SHG signal related to the electrical properties of the sample, wherein features from the SHG signal are extracted using a transform; and correlating the extracted features to one or more electrical properties of the sample.

In various embodiments, the extracted features can include spatio-temporal intensity of the SHG signal. In various embodiments, the transform can comprise at least one of: a Fourier transform, a wavelet or a machine learning kernel. In various embodiments, correlating the extracted features can include under the control of the hardware computing device: decoding the extracted features using a decoder; mapping the decoded extracted features onto a decision; and classifying the SHG signal based on the decision.

In various embodiments, the decision can include presence or absence of metal contaminant. In various embodiments, the decision can include at least one of: presence of metal contaminant, absence of metal contaminant, type of contaminant, or amount of metal contaminant. The decoder can be a linear or a nonlinear decoder.

In various embodiments, mapping the decoded extracted features onto a decision can comprise projecting the extracted features onto a decision boundary. The decision boundary can be obtained during a training phase of the automated system. In various embodiments, the automated method can further comprise under the control of the hardware computing device: removing a portion of the SHG signal attributed to one or more material properties of the sample. In various embodiments, the portion of the SHG signal attributed to one or more material properties of the sample can be removed prior to extracting features from the SHG signal. In various embodiments, removing the portion of the SHG signal attributed to one or more material properties of the sample can include receiving data associated with one or more material properties of the sample; determining a quantitative relationship between the received data associated with one or more material properties of the sample and the received signal; and normalizing the received signal to remove the portion of the SHG signal attributed to one or more material properties of the sample. In various embodiments, data associated with one or more material properties of the sample can be received from using a secondary semiconductor analysis device.

BRIEF DESCRIPTION OF THE DRAWINGS

The figures schematically illustrate aspects of various embodiments of different inventive variations.

FIG. 1A is a diagram of an embodiment of a SHG metrology system. FIGS. 1B and 1C depict that the layer thickness of the wafer correlates strongly and directly with the maximum SHG signal at any given point as observed from the crescent motif of FIG. 1C.

FIG. 4A depicts the maximum SHG signal obtained across a wafer using an embodiment of a SHG metrology system and a reflectometer. FIG. 4B depicts the device layer thickness across the wafer. FIG. 4C depicts the corrected maximum SHG signal across the wafer obtained by taking into account variations in the device layer thickness. The corrected maximum SHG signal can be obtained by dividing the maximum SHG signal at each point by expected maximum SHG signal at that point given a thickness of the layer at that point.

FIGS. 6A-6D depict the maximum SHG signal wafer maps of wafers having known levels of surface Cu contamination. FIG. 6A depicts the maximum SHG signal for a control wafer. FIG. 6B depicts the maximum SHG signal for a 200 mm 1500/1000 nm SOI wafer spin-coated with a Cu contamination level of 1E10 atoms/cm$^2$. FIG. 6C depicts the maximum SHG signal for a 200 mm 1500/1000 nm SOI wafer spin-coated with a Cu contamination level of 1E11 atoms/cm$^2$. FIG. 6D depicts the maximum SHG signal for a 200 mm 1500/1000 nm SOI wafer spin-coated with a Cu contamination level of 1E12 atoms/cm$^2$.

FIG. 8 depicts an embodiment of a system architecture comprising a SHG metrology characterization module that is configured to normalize the SHG signals by taking into account the device layer thickness.

FIG. 10 is a flowchart that illustrates a method of providing an output from an embodiment of a SHG metrology system.

FIG. 11 is a flowchart that depicts a method of providing an output from an embodiment of a SHG metrology system in a supervised training mode.

FIG. 12 is a flowchart that depicts a method of providing an output from an embodiment of a SHG metrology system in a supervised testing mode.

FIG. 13 is a flowchart that depicts a method of providing an output from an embodiment of a SHG metrology system in an unsupervised training mode.

FIG. 14 is a flowchart that depicts a method of providing an output from an embodiment of a SHG metrology system in an unsupervised testing mode.

FIG. 17 illustrates a method of estimating the SHG signal data classification accuracy using signal detection theory.

DETAILED DESCRIPTION

Figures 1B, 1C:
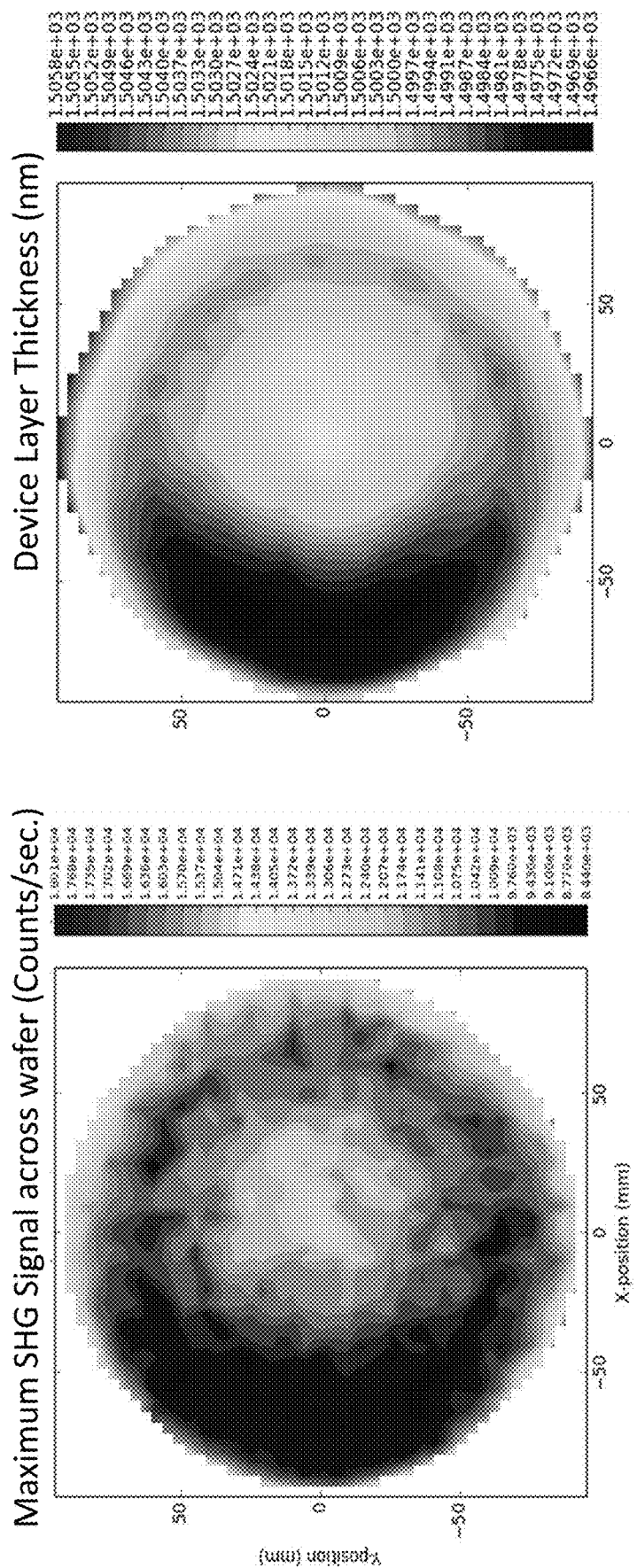
FIGS. 1B and 1C depict results obtained for a wafer using an embodiment of a SHG metrology system and a reflectometer. The Wafer is uncontaminated 200 mm 1500/1000 nm SOI.

FIG. 1A is a diagram of a system 2100 as may employed in connection with the subject methodology. The system includes a primary laser 2010 for directing a primary beam 2012 of electro-magnetic radiation at a sample wafer 2020, which sample is held by a vacuum chuck 2030. The chuck 2030 includes or is set on x- and y-stages and optionally also a rotational stage for positioning a sample site 2022 across the wafer relative to where the radiation is directed. A beam 2014 of reflected radiation directed at a detector 2040 will include an SHG signal. The detector may be any of a photomultiplier tube, a CCD camera, an avalanche detector, a photodiode detector, a streak camera and a silicon detector. The sample site 2022 can include one or more layers. The sample site 2022 can comprise a composite substrate including at least two layers. The sample site 2022 can include an interface between two dissimilar materials (e.g., between two different semiconductor materials, between two differently doped semiconductor materials, between a semiconductor and an oxide, between a semiconductor and a dielectric material, between a semiconductor and a metal, between an oxide and a metal, between a metal and a metal or between a metal and a dielectric).

Various embodiments of the system 2100 can include one or more shutter-type devices 2050. These are employed as described in connection with the methodology below. The type of shutter hardware used will depend on the timeframe over which the laser radiation is to be blocked, dumped or otherwise directed away from the sample site.

An electro-optic blocking device such as a Pockel's Cell or Kerr Cell can be used to obtain very short blocking periods (i.e., with switching times on the order of 10-9 to 10-12 seconds). For longer blocking time intervals (e.g., from about 10-5 seconds and upwards) mechanical shutters or flywheel chopper type devices may be employed.

Electro-optic blocking devices can provide a wider range of materials to be tested in accordance with the methods below. A photon counting system 2044 capable of discretely gating very small time intervals, typically, on the order of picoseconds to microseconds can be also be included to resolve the time-dependent signal counts.

In various embodiments of the system 2100 an additional radiation source (for example, a laser illustrated emitting a directed beam or a UV flash lamp emitting a diverging or optically collimated or a focused pulse) may also be incorporated in the system 2100 to provide such features as referenced above in connection with the portion of U.S. Provisional Application No. 61/980,860, filed on Apr. 17, 2014, titled "Wafer Metrology Technologies," referred to as Section I entitled "Pump and Probe Type SHG Metrology," which is incorporated herein by reference in its entirety and/or initial charging/saturation in the methods below. See also co-pending U.S. patent application Ser. No. 14/690,179, filed Apr. 17, 2015 titled "Pump and Probe Type Second Harmonic Generation Metrology", which is incorporated herein by reference in its entirety.

Various other hardware devices and systems can be used to push the methods into faster-yet time frames. For example, various embodiments of the system 2100 can include delay line hardware. The delay line can be a variable delay line which can advantageously allow multiple transient charge decay interrogation events on a time frame ranging from immediately (although delay of only $10^{-12}$ seconds may be required for many methodologies) to tens of nanoseconds. In some embodiments, beam splitting and switching (or shuttering on/off) between a plurality of set-time delay lines can be used to allow a number of time-delayed interrogation events.

In various embodiments of the system 2100, the beam 2012 from the laser 2010 can be split by a beam splitter between two optical paths. The beam splitter can be configured to split the beam 2012 unequally between the two optical paths. For example, 70% of the energy of the beam 2012 can be directed along a first optical path (and 30% of the energy of the beam 2012 can be directed along a second optical path. As another example, 60% of the energy of the beam 2012 can be directed along the first optical path and 40% of the energy of the beam 2012 can be directed along the second optical path. As yet another example, 80% of the energy of the beam 2012 can be directed along the first optical path and 20% of the energy of the beam 2012 can be directed along the second optical path. The beam splitter can comprise a dielectric mirror, a splitter cube, a metal coated mirror, a pellicle mirror or a waveguide splitter. In implementations, where the beam 2012 includes optical pulses, the beam splitter can include an optical component having negligible dispersion that splits the beam 2012 between two optical paths such that optical pulses are not broadened. The beam travelling along one of the first or the second optical paths can be configured as a pump beam and the other can be configured as a probe beam. In those embodiments in which the beam splitter is configured to split the beam 2012 unequally between the first and the second optical paths, the beam having a larger amount of optical energy can be configured as the pump beam and the beam having a smaller amount of optical energy can be configured as the probe beam. The optical path along which the probe beam travels can be lengthened or shortened to change its arrival timing relative to the pump beam. In various embodiments, fiber optics can be employed in the first or the second optical paths to introduce optical delay between the pump and the probe beams (e.g., as presented in U.S. Pat. No. 6,819,844 incorporated herein by reference in its entirety for such description). In various embodiments, the first and the second optical paths can be angled with respect to each other such that the pump and probe beams are incident on the sample wafer at different angles. Such an approach can facilitate measuring pump and probe SHG responses separately. In such cases, two detectors may be advantageously employed for detecting SHG responses from the pump and the probe beams.

Referring to FIG. 1A, the output from the detector 2040 and/or the photon counting system 2044 can be input to an electronic device 2048. The electronic device 2048 can be, for example, a computing device, a computer, a tablet, a microcontroller or a FPGA. The electronic device 2048 can include a processor or processing electronics that may be configured to execute one or more software modules. In addition to executing an operating system, the processor may be configured to execute one or more software applications, including a web browser, a telephone application, an email program, or any other software application. The electronic device 2048 can implement the methods discussed herein by executing instructions included in a machine-readable non-transitory storage medium, such as a RAM, ROM, EEPROM, etc. The electronic device 2048 can include a display device and/or a graphic user interface to interact with a user. The electronic device 2048 can communicate with one or more devices over a network interface. The network interface can include transmitters, receivers and/or transceivers that can communicate over wired or wireless connections.

The system 2100 can include one or more optional optical components. For example, the system 2100 is shown including a dichroic reflective or refractive filter 2080 for selectively passing the SHG signal coaxial with reflected radiation directly from the laser 2010. Alternatively, a prism may be employed to differentiate the weaker SHG signal from the many-orders-of-magnitude-stronger reflected primary beam. Other options include the use of diffraction grating or a Pellicle beam splitter. As shown in system 2100, an optical bundle 2082 of focusing and collimating/collimation optics may be provided. In various embodiments of the system 2100 additional optical components, such as for example one or more optical filters, zoom lens and/or polarizers may be included. Also, an angular (or arc-type) rotational adjustment (with corresponding adjustment for the detector 2040 and in-line optical components) can also be included in some embodiments.

Referring to the system 2100, laser 2010 may operate in a wavelength range between about 700 nm to about 2000 nm with a peak power between about 10 kW and 1 GW, but delivering power at an average below about 100 mW. In various embodiments, average powers between 10 mW and 10W should be sufficient. In embodiments including an additional light source (e.g., another laser or a flash lamp) configured as a pump source may operate in a wavelength range between about 80 nm and about 800 nm delivering an average power between about 10 mW and 10 W. Values outside these ranges, however, are possible.

In various embodiments, since an SHG signal is weak compared to the reflected beam that produces it, it may be desirable to improve the signal-to-noise ratio of SHG counts. As photon counting gate times decrease for the blocking and/or delay processes described herein, improvement becomes even more useful. One method of reducing noise that may be employed is to actively cool the detector. The cooling can decreases the number of false-positive photon detections that are generated randomly because of thermal noise. This can be done using cryogenic fluids such as liquid nitrogen or helium or solid state cooling through use of a Peltier device. Others areas of improvement may include use of a Marx Bank Circuit (MBC) as relevant to shutter speed.

A SHG metrology characterization module uses inputs from the ancillary techniques to parse material properties via physically derived machine learning models from within the measured SHG signal, while providing a smaller footprint, reducing cost, and increasing throughput. The system allows for the extraction of independent semiconductor and material properties from the unparsed SHG signals. Stated otherwise, embodiments hereof employ integration of additional characterization techniques such as those aforementioned with the non-destructive characterization abilities of SHG metrology, enhanced by a suite of physically derived machine learning models to interpret SHG signals as a portfolio of independent wafer properties, such as layer material layer thickness variation, defect and contaminant.

SHG based metrology systems can be useful for measuring semiconductor wafer parameters, such as but not limited to local surface and subsurface metal and organic contamination, trap charge density, strain, and doping levels. Sets of samples have been made with controlled levels of contaminant or defect in order to assess and verify the sensitivity of SHG. SHG signal level shows clear contrast between controlled samples in this context.

However, SHG readings from existing SHG based metrology systems can become much more complicated when evaluating real-world samples with unknown types and levels of defect and material properties. For example, it presently involves substantial expert interpretation based on measured SHG signal alone to estimate whether a variation in SHG signal across a wafer is due to an electrical defect or a material property variation. To improve materials failure analysis and select correct wafers for further processing, additional (oftentimes destructive) efforts are undertaken to parse SHG signals.

In developing a system to parse material properties from within the measured SHG signal, the effect of the material properties of the sample wafer (e.g. thickness of one or more layers of the sample wafer) on the SHG signal was unexpectedly discovered. It was observed that variations in the thickness of one or more layers of the sample wafer can oftentimes camouflage SHG signal changes from industrially relevant contamination and wafer defect, leading to false positive identification of industrially problematic material. It was observed that SHG signal variance from acceptable layer variations can be on the same order of magnitude as signal variance from unacceptable levels of material contamination or defect. Unparsed monitoring of an SHG signal across a material with no consideration for layer thickness variations, can make it difficult to detect and differentiate changes in SHG signal caused by layer thickness variations versus changes in SHG signal due to industrially relevant levels of electrically active contamination or structural defect.

As an example, a batch of four SOI wafers from a leading manufacturer were selected for intentional contamination, to show the efficacy of SHG in characterizing varying levels of surface metals. When the wafers were characterized via SHG, there was a much larger variance of SHG signal within each wafer than between the wafers leading to ambiguity between the samples. Four wafers were used: one as a control, and three contaminated at levels of 1E10, 1E11, and 1E12 atoms Cu/cm2 respectively. As seen in FIG. 1B, relying on unparsed SHG signal levels made it difficult to tell good from bad wafers.

When measurements had first been taken and analyzed, it was thought that the experiment was a failure. As a result of this problem, the ensuing work directed towards parsing SHG signals uncovered that the experiment was not a failure, but that another undetected problem existed.

Information provided by the vendor regarding the sample wafers that were tested indicated a uniform device layer thickness of 1500 nanometers. However, when additional measurements of the sample wafer obtained using a secondary analysis device including but not limited to: a spectroscopic ellipsometer (SE), a reflectometer, a CV-IV parametric analyzer, an Inductively Coupled Plasma Mass Spectrometry (ICPMS), Vapor Phase decomposition (VPD)-ICPMS, a Total Reflection X-Ray Fluorescence (TXRF), a Secondary Ion Mass Spectrometry (SIMS), a Rutherford Backscattering (RBS), a Scanning/Tunneling Electron Microscope (SEM/TEM), an Atomic Force Microscope (AFM), a Brightfield/Darkfield Microscopy, a Glow Discharge Optical Emission Spectroscopy (GD-OES), an X-Ray Photoelectron Spectroscopy ( )PS), a Fourier Transform Infrared Spectroscopy (FTIR), or a microwave detected photoconductive decay (μ-PCD) indicated that the device layer was not uniform, as seen in FIG. 1C. In various embodiments, the secondary analysis device can be separate from and/or distinct from the SHG metrology system. Upon the generation of extensive layer thickness maps and side-by-side comparison with SHG map, the strong influence of layer thickness variation on SHG measurement was discovered. For example, both the device layer thickness map of FIG. 1C and the SHG signal map of FIG. 1B indicate a crescent shape. This discovery was unexpected, as it was extraordinary that such a large SHG variance was being caused by a variance in layer thickness.

Specifically, the side-by-side comparisons of the SHG signal map and the device layer thickness map indicated that variations of only 10 nm in a 1500 nm thick device layer (less than 0.7% variance) are correlated with a more than 30% difference in SHG signal levels. This is a very large change that is not expected or easily explained by simple thin film interference effects with the 800 nm fundamental signal.

Indeed, layer thickness variations made it impractical to note the difference between wafer samples contaminated with copper at concentrations of 1E+10 and 1E+11 atoms/cm2 on the surface, and a control wafer with no copper added as evident in comparing FIGS. 6A-6D. However, as shown in FIGS. 7A-7D, once the samples were normalized for layer thickness effects the differences between the varying contaminant levels and control sample became readily visible and statistically relevant.

Figure 2:
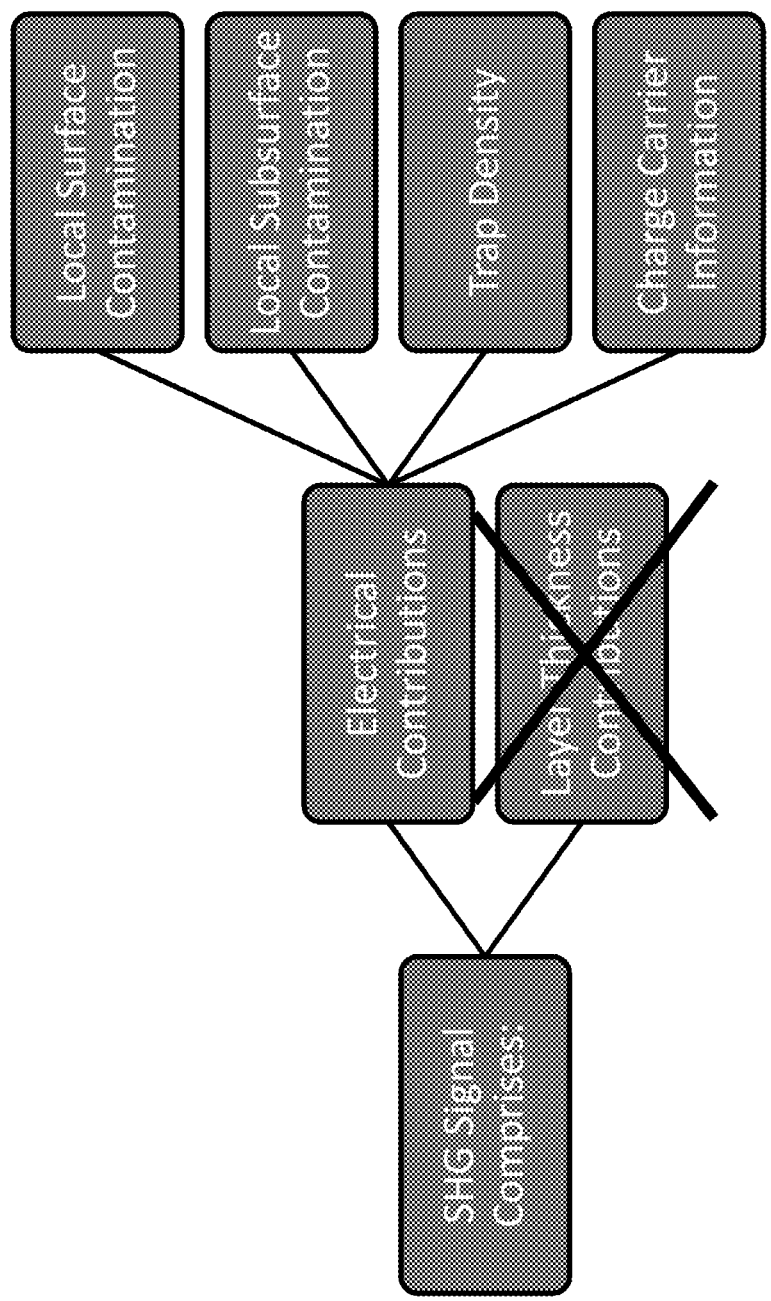
FIG. 2 depicts a method of decoupling SHG signal from layer thickness

As noted in FIG. 2, SHG signal from a sample wafer obtained using a SHG metrology system can include contributions from electrical properties of the sample wafer including but not limited to local surface contamination, local subsurface contamination, trap density and/or charge carrier information. Additionally, as discussed above, the SHG signal also includes contribution from one or more material properties including but not limited to variation in thickness of one or more layers of the sample wafer and/or presence of a known artifact. In addition, the SHG signal can also include contribution from structural defects. The embodiments disclosed herein are configured to parse the obtained SHG signal to remove contribution from one or more material properties of the sample wafer including but not limited to variation in thickness of one or more layers of the sample wafer and/or presence of a known artifact and isolating the contribution to SHG signal from electrical properties of the sample wafer and/or structural defects.

Such "parsed" or "de-cloaked" SHG measurements enabled distinguishing between the levels of contamination on wafers that would fail in later processing steps versus good wafers, while providing the benefit of layer thickness measurements simultaneously through SHG.

Accordingly, the problem of SHG signal parsing or defect de-cloaking can involve integrating information about layer thickness and the other techniques referenced alongside the spatio-temporal SHG signal. The subject embodiments thereby address the challenge of signal interpretation by including additional characterization techniques inside the SHG metrology module, and using physically derived machine learning models to parse the SHG signal based on corresponding measurements. This ability can be extended to other material properties and analysis techniques, as described below including: SE/reflectometry, CV-IV, TXRF, Vapor Phase decomposition (VPD)-ICPMS, μ-PCD, Rutherford Backscattering (RBS), a Scanning/Tunneling Electron Microscope (SEM/TEM), Atomic Force Microscope (AFM), Brightfield/Darkfield Microscopy, Glow Discharge Optical Emission Spectroscopy (GD-OES), X-Ray Photoelectron Spectroscopy ( )PS), Fourier Transform Infrared Spectroscopy (FTIR), and time of flight (TOF)-SIMS that are based on metrology which are widely used in semiconductor fabrication plants, commonly referred to as fabs.

The subject method proceeds by first performing measurements on the test sample in question (a "scan") using the integrated hardware. These measurements could then be used in conjunction with a suite of mathematical algorithms to interpret unprocessed SHG measurements.

FIG. 8 illustrates the overall system architecture. SHG signals are acquired using the hardware platform and analyzed in a computer using a suite of machine learning tools. Signals using other traditional metrology tools can enhance the performance of system as tutor signals for the machine learning algorithms. Over a term of use, correlating the results of SHG metrology with these tools will enable the SHG metrology tool to "learn" characteristics in the SHG signal counts pertaining to commercially relevant parameters.

Figure 9:
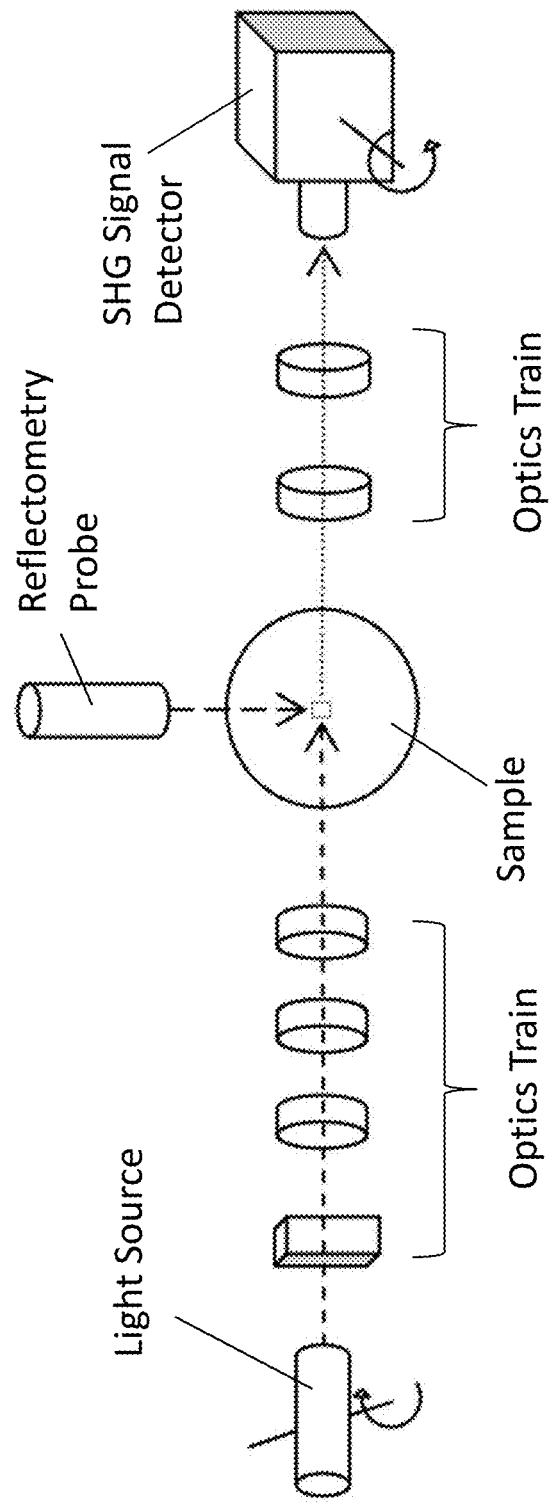
FIG. 9 depicts an embodiment of a system comprising a SHG metrology system in conjunction with a reflectometer.

In one variation, as shown in FIG. 9, a reflectometer is used in conjunction with the SHG apparatus to identify and isolate the portion of SHG signal variation that is due to layer thickness variations in multilayer materials. The SHG and layer thickness maps are combined using a physically derived machine learning model to learn what the normal contribution of layer thickness is for a given material system. Embodiments of the system illustrated in FIGS. 1A and/or FIG. 9 can additionally or alternatively include hardware computing devices that use embodiments of the machine learning methodologies and techniques described herein and illustrated in FIGS. 11-17 to, for example, parse or classify SHG signal data based on electrical properties of the sample wafer.

Figure 3:
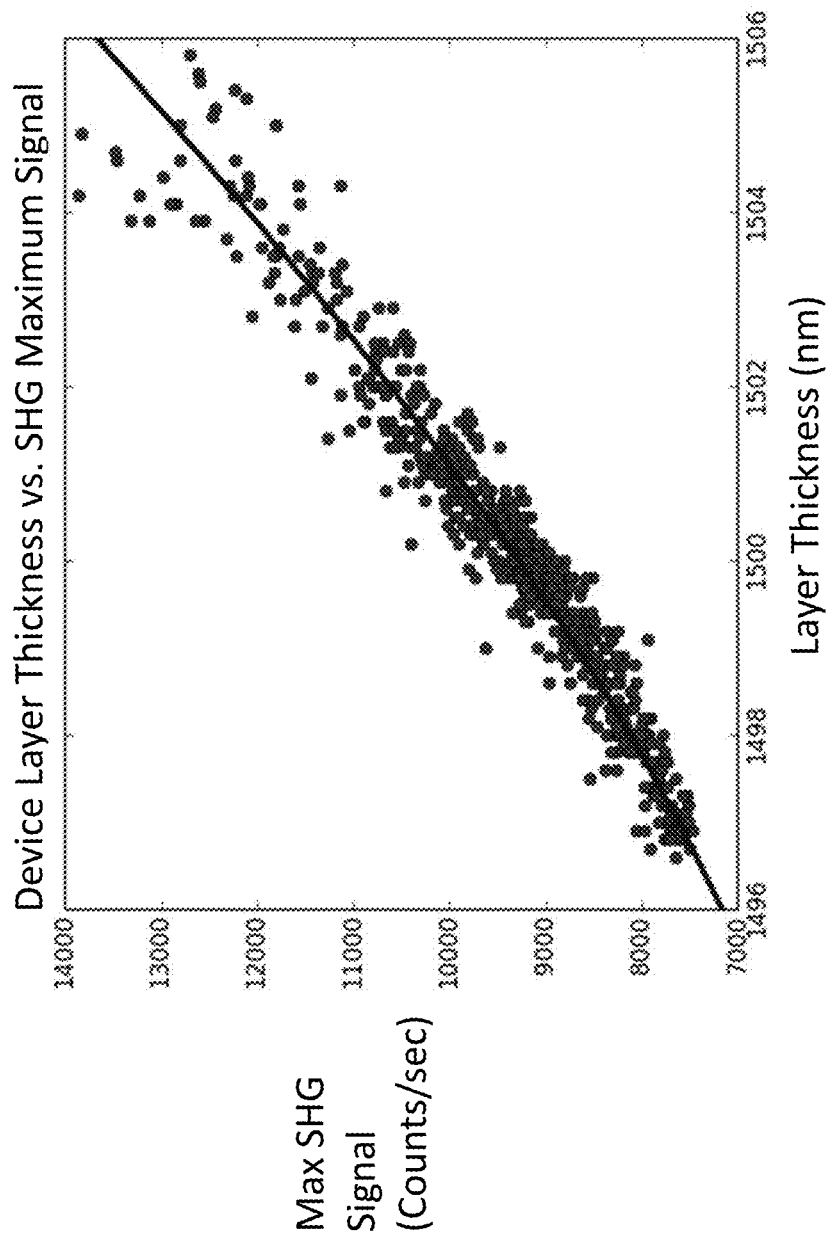
FIG. 3 illustrates a plot that establishes quantitative relationship between Device Layer Thickness and SHG Max Signal. A $3^{rd}$ order polynomial curve is fit to the obtained Max SHG signal to account for the curvature of the distribution of the SHG Max Signal with respect to the Device Layer Thickness. The distribution of the SHG Max Signal with respect to the Device Layer Thickness is nonlinear as indicated by the $3^{rd}$ order polynomial curve having coefficients a=−1.78e−01, b=8.87e+02, c=−1.47e+06, d=8.16e+08.
Figures 5A, 5B:
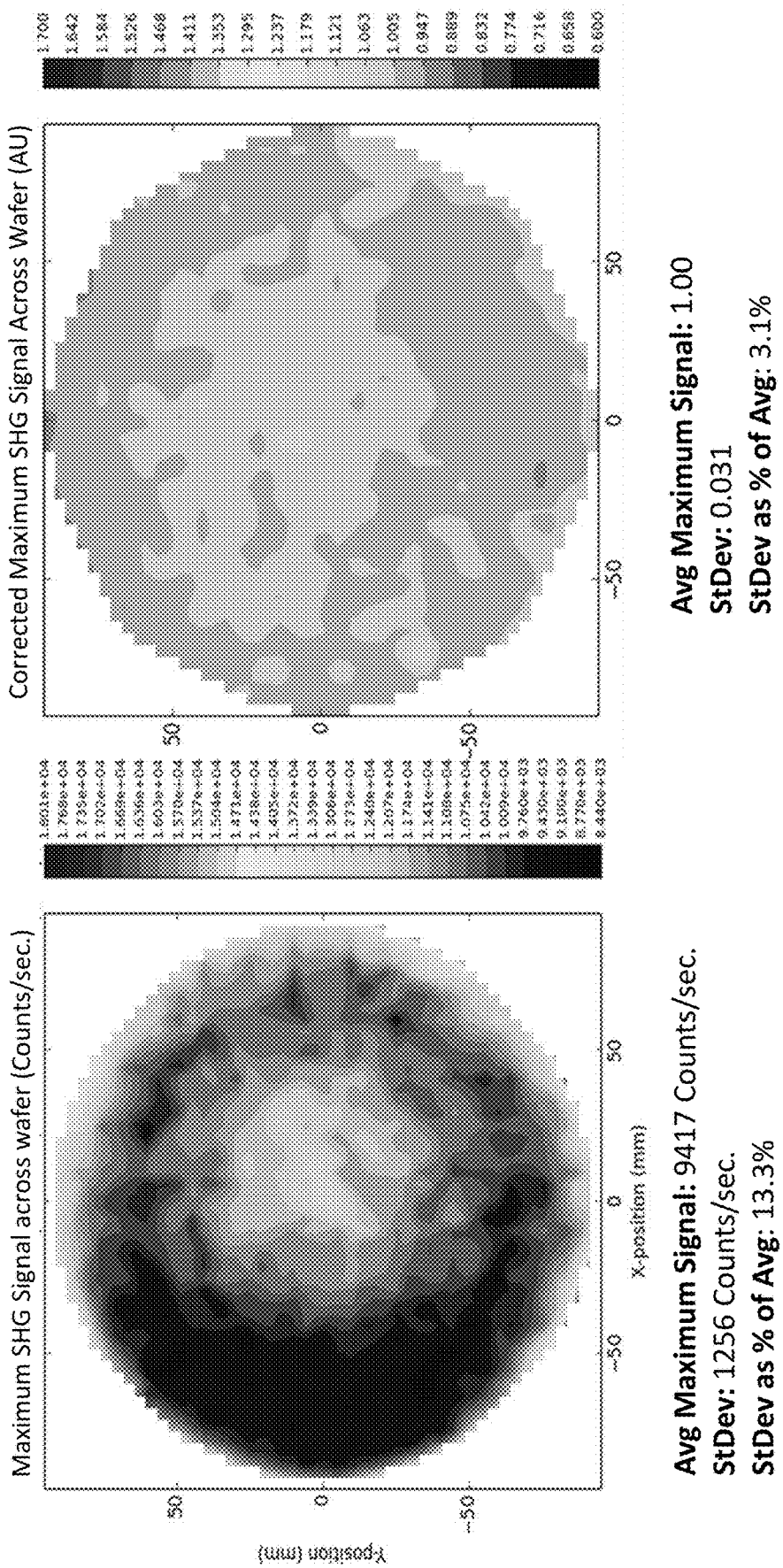
FIGS. 5A and 5B depict the statistical comparison of the maximum SHG signal before and after correction. The maps reflect that the wafer is expected to be without major complications. The maps also reflect that the intra-wafer variability due to layer thickness is reduced.
Figures 7A, 7B, 7C, 7D:
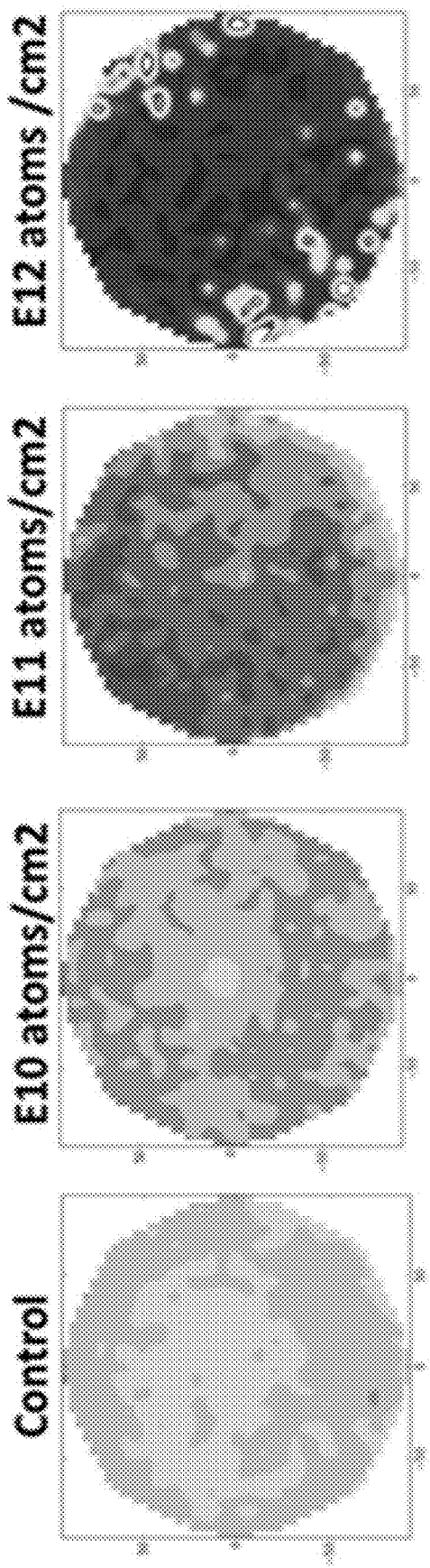
FIGS. 7A-7D depict the maximum SHG signal maps normalized by taking into account layer thickness effects corresponding to the maps depicted in FIGS. 6A-6C.

For 1500/1000 nm SOI material, reflectometer measurements were compared to SHG measurements at identical points across sample wafers, and a quantitative relationship deduced between the device layer thickness and the maximum SHG signal obtained at each of these identical points is shown in FIG. 3.

The quantitative relationship demonstrated in FIG. 3 was used to divide the SHG signal at each point by the expected SHG given the device layer thickness in order to control for the layer thickness effects and produce an SHG mapping of the wafer from which material thickness has been removed as a variable. This approach allows further signal analysis methods to determine electrical properties of the material from the SHG signal without the camouflaging effect of layer thickness described in the problem statement. As automated by virtue of physically derived machine learning models, materials can be characterized by correlation with any secondary analysis technique with minimal user input.

Such physically derived machine learning models concern the following aspects of wafer properties, although is not limited thereto: layer thickness, artifact detection, artifact identification and artifact quantification. In addition, the commercial need for in-line tools also requires efficient computational algorithms to achieve in-situ results for materials characterization.

FIG. 10 depicts an SHG characterization module. The general architecture for the machine learning comprises a training module and testing module. The training module takes SHG signals and tutor signals (optional) as input, depending on whether the machine learning technique is supervised or unsupervised. The training module generates output that is consequently evaluated using the signal detection theory, which measures the performance of the training module. After reaching certain level of satisfactory performance, new SHG signals can be passed through the testing module, which gives out a predicted layer thickness and/or information about wafer defects. Two types of training modules are described on the basis of whether the selected module is for supervised learning or unsupervised learning.

FIG. 11 illustrates a supervised learning mode, where both SHG signals and tutor signals are fed into the SHG characterization module as input. Within the SHG characterization module, an iterative algorithm is employed and numerical optimization is required. A forward model is devised to describe the relationship between SHG signals and ground truth response, such as layer thickness and metal defect, which can be extracted by tutor signals. A loss function is constructed based on the discrepancy between the predicted response and the ground truth response. A numerical optimization is performed through an iterative procedure to obtain the desirable model parameters that minimize the loss function. Stopping criteria are employed to terminate the optimization procedure. Once optimal solution for the model parameters is reached, the model parameters can be output for the testing mode. As shown in FIG. 12, under the supervised testing mode, the testing module gets input from the optimal model parameters and new SHG signals, and parses out information pertaining to wafer properties as output, such as layer thickness and various defects.

FIG. 13 illustrates the unsupervised learning mode, where the training module takes only SHG signals as input. An iterative procedure is administrated, where a forward model is devised and the ultimate goal is to identify region of interest (ROI) and signal characteristics (such as single curve characterization), while correlation between SHG signals and other destructive signals becomes the judge for the learning system. As shown in FIG. 14, under the unsupervised testing mode, one uses the identified ROI and characteristics to parse information on new SHG signals.

Notably, wafer properties can be roughly categorized into three categories: layer thickness, artifact detection and artifact identification. The machine learning methodologies for each category may differ as discussed below.

Layer Thickness:

Supervised learning may be used to characterize layer thickness. SHG signals will be measured on samples with known thickness, whereas the ground truth for layer thickness can be obtained via other existing techniques. Supervised learning algorithms will be used to map out the function between input (SHG signals) and output (layer thickness). Such supervised learning algorithms include linear regression, nonlinear regression, and neural network. Choices of algorithms will depend on the nature and manufacturer of different wafers. The supervised learning architecture is trained until it reaches certain accuracy, which can be quantified using signal detection theory, for instance the receiver operator characteristic (ROC) curve. After that, layer thickness can be predicted based on SHG signals measured on new samples.

Artifact Detection:

SHG signals may be collected from control wafers (without artifact) and target wafers (with artifact) for training purposes. Features will be extracted from the SHG signals using a variety of transforms, including but not limited to, using the original signal, Fourier transform, wavelet, kernel-based methods, a machine learning kernel (e.g., a Fisher kernel, a graph kernel, a polynomial kernel, a RBF kernel, a string kernel) or any feature extraction technique. A sparse logistic regression and/or sparse support vector machine will be employed to correlate the extracted features with wafer conditions (artifact or not). The learned weights are stored in the computer for future prediction. Once the training reaches certain accuracy, SHG signals are collected for the new wafer and prediction made as to whether or not it has an artifact based on a forward model that uses the learned weights and input SHG signals.

Artifact Identification:

A series of wafer samples may be identified and constructed based on industrial needs, which have certain known artifacts. Information about the artifact type and spatial location will be obtained. SHG signals will be measured on these samples. Similarly to artifact detection, features will be extracted from the SHG signals using a variety of transforms, including but not limited to, using the original signal, Fourier transform, wavelet, kernel-based methods, a machine learning kernel (e.g., a Fisher kernel, a graph kernel, a polynomial kernel, a RBF kernel, a string kernel) or any feature extraction technique. A multinomial training model will be employed to accommodate different types of artifact, and a sparse logistic regression and/or sparse vector machine will be trained using the multinomial model. Such a model will learn a mapping from input (SHG signals) to output (artifact type). The learned weights will be stored in the computer for future prediction. Once the training reaches certain accuracy, SHG signals may be collected for the new wafer and prediction of the specific artifact type based on a forward model that uses the learned weights and input SHG signals.

Finally, a portfolio of machine learning methodologies (per a Forward Model Methodology) targeted for wafer characterization herein or hereby is summarized below:

|  | Loss Function | Machine Learning |
| --- | --- | --- |
| Layer Thickness | Square norm | Ridge Regression |
|  | Square norm | LASSO |
|  | Square norm | Neural network |
| Contamination Detection | Logistic loss | L2-regularized logistic regression |
|  | Logistic loss | L1-regularized logistic regression |
|  | Hinge loss | Support vector machine |
| Contamination Identification | Multinomial logistic loss | Multinomial logistic regression |
|  | Multi-class hinge loss | Multi-class support vector machine |
|  | Zero one loss | Deep learning |

In accordance with these variations and others as described above, many implementations are possible according to devices, systems, methods (including software and associated hardware for carrying out specified acts) and UI features (including layouts and options and/or methodology associated with system use).

In various embodiments, machine learning methodologies can be employed to classify parsed SHG signal maps. Automated hardware systems can be employed to classify various parsed SHG signal maps based on the presence or absence of contaminants, the amount of contaminants or other electrical and structural characteristics that may be relevant from an industrial perspective. Embodiments of such automated hardware systems can be additionally or alternatively be included with embodiments of semiconductor metrology based systems and devices including but not limited to embodiments of the systems illustrated in FIGS. 1A and 9. In various embodiments, depending on the composition of the sample wafer, parsing of the SHG signal obtained from the wafer may be omitted and the obtained SHG signal can be used by the automated hardware systems to classify the sample wafer. For example, parsing of the obtained SHG signal to remove contributions to the SHG signal from variations in thickness of one or more layers can be omitted if the sample wafer comprises a bulk material, such as, for example, Si. However, if the sample wafer comprises hetero-interface materials, such as, for example SOI, then the obtained SHG signal can be parsed to remove contributions to the SHG signal from variations in thickness of one or more layers as discussed above. For example, SHG signal from hetero-interface materials, such as, for example SOI, can be parsed to remove layer thickness effects by (a) collecting layer thickness data using a correlative technique such as, for example, surface reflectivity (SR) or SE; and (b) establishing a mathematical relationship between the obtained SHG signal and the layer thickness data (e.g., a $3^{rd}$ order polynomial curve).

Figure 15:
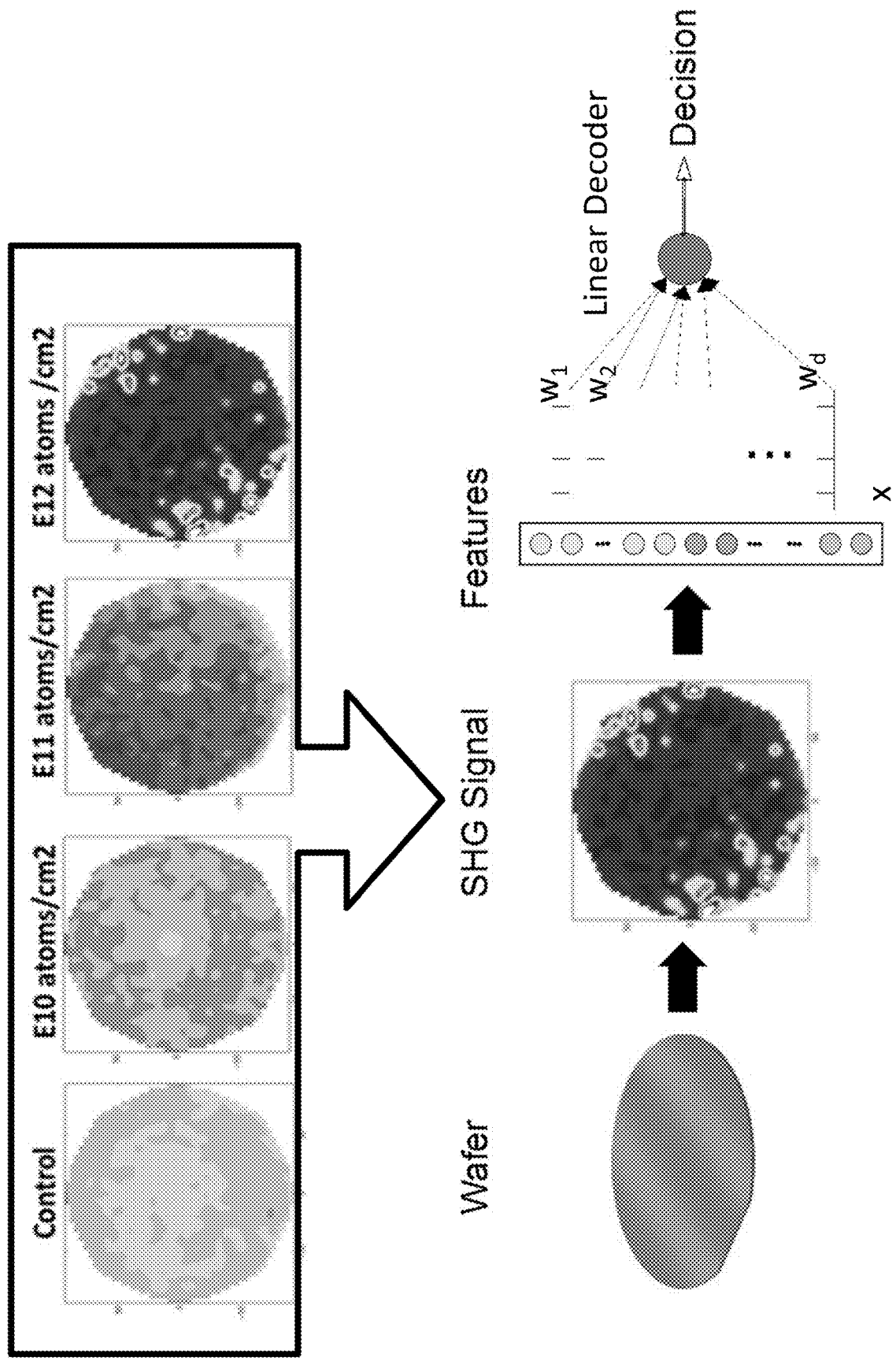
FIG. 15 illustrates a method of classifying obtained SHG signal data.

Classifying a SHG signal map can include extracting features from the SHG signal map; decoding the extracted features using a decoder; making a decision based on the output of the decoder; and classifying the SHG signal map based on the decision. This method is illustrated in FIG. 15.

The parsed (or unparsed) SHG signal output for various portions of the sample wafer (also referred to herein as SHG signal map) can be processed to extract features. For example, the SHG signal map can be fed through certain types of kernels to extract features. For example, features can be extracted by using a variety of transforms including but not limited to using the original signal, Fourier transform, wavelet, kernel-based methods, a machine learning kernel (e.g., a Fisher kernel, a graph kernel, a polynomial kernel, a RBF kernel, a string kernel) or any feature extraction technique. Depending on the type of kernel, the extracted features can be a feature vector (as shown in FIG. 15) or a feature matrix. In various embodiments, such features can be spatial-temporal intensity of the SHG signal. In another embodiment, the features can be based on or extracted from a Fourier transform of the SHG signal. A decoder is applied on the aforementioned extracted features in order to map the signal to the decision, the decision being the label of the data. For example, such a decision can encode whether or not the wafer has metal contamination. The decoder can be either linear or nonlinear, depending on the applications. The decoder can be trained based on an ensemble of SHG signals together with training labels (also referred to herein as ground truth). The decoded extracted features (also referred to herein as testing data) can be projected onto a decision boundary obtained from training the decoder. By projecting the decoded extracted features a decision which corresponds to the training labels can be made. The SHG signal map can be classified based on the decision. For example, in some embodiments, the training label can be presence or absence of metal contamination in the sample wafer. In such embodiments, based on the decoding of the extracted features a decision can be made whether the obtained SHG signal map should be classified as having metal contamination or not having metal contamination.

Signal detection theory can be used to quantify classification accuracy in terms of true positive rate vs. false positive rate. Standard cross validation can be used to assess the classification accuracy. In various embodiments, different models including but not limited to logistic regression, L1-regularized logistic regression, support vector machine, sparse support vector machine, neural network or deep learning and different solvers including but not limited to iterative shrinkage, gradient descent, interior point method, hybrid iterative shrinkage or linearized Bregman can be employed to train the decoder.

Figure 16A:
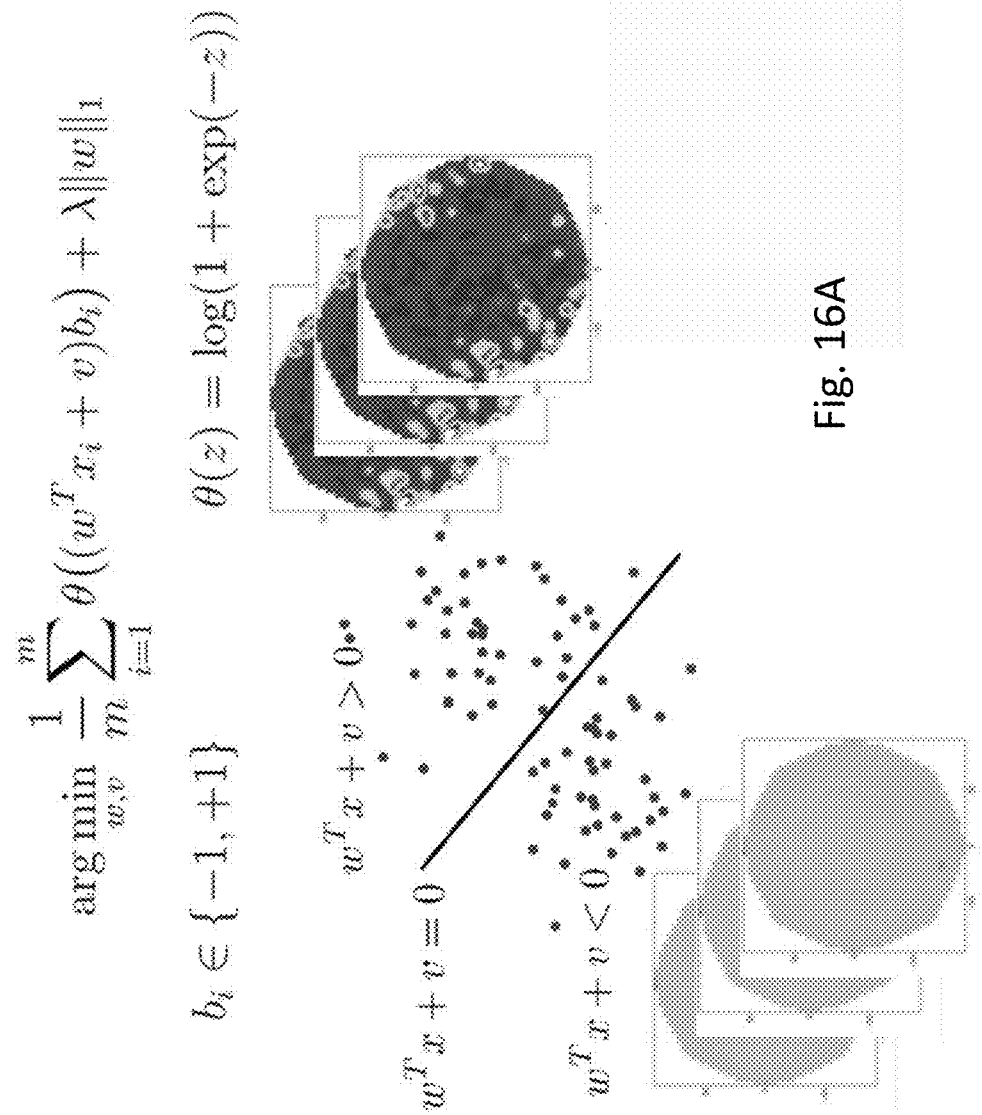
FIG. 16A illustrates a method of classifying obtained SHG signal data using an automated hardware system including a linear decoder.
Figure 16B:
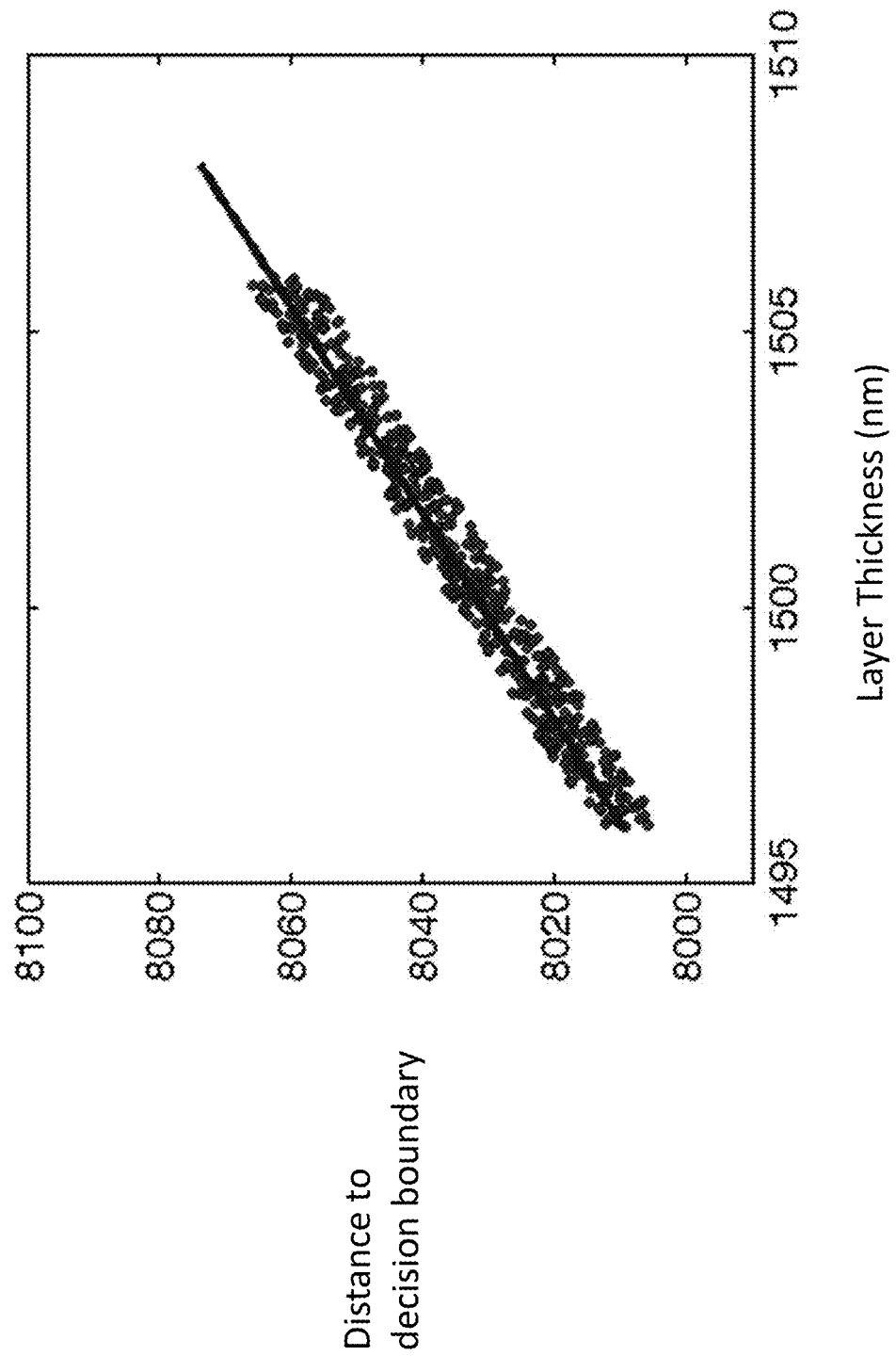
FIG. 16B illustrates a plot of distance to decision boundary of the SHG data signals projected on the hyperplane $w^T x$ obtained during training phase of the automated hardware system including a linear decoder.

FIG. 16A illustrates a method of classifying the obtained SHG signal map using an automated hardware device including a linear decoder. In some embodiments, the automated hardware device can be used to train the system to classify obtained SHG signal maps according to particular quantity and/or species of metal contaminants as compared to a control sample. In various embodiments, the obtained SHG signal maps can be classified by taking into account and deconvoluting in a quantified fashion structural aspects such as layer thickness variation. In various embodiments, the linear decoder can be modeled as L1-regularized logistic regression, which automatically selects features that are informative about the decision boundary that can be geometrically interpreted as a hyperplane in the feature space.

As discussed above, the features extracted from the obtained SHG signal maps are projected onto a decision boundary obtained from training the automated system. For the automated system including a linear decoder, the projection onto a decision boundary includes projection onto a trained hyperplane $w^Tx$. The decision boundary obtained from training the automated system including a linear decoder is indicated by the solid line in FIG. 16B and the closed circles indicate the projected data. A decision can be made based on the distance from the decision boundary.

In various embodiments, the obtained SHG signal data can be mapped into a projection vector, which clusters the obtained SHG signals into two or more decisions. Signal detection theory can be used to estimate the SHG signal data classification accuracy, as shown in FIG. 17. For example, signal detection theory can be used to visualize true positive rate (TPR) vs false positive rate (FPR). The area under the receiver operator characteristic (ROC) curve can be used to determine the classification accuracy.

As a further example an automated system configured to parse SHG signal data to extract features from the SHG signal data and correlate the extracted features to one or more electrical properties of a sample wafer (e.g., presence or absence of contaminants, amount and/or species of contaminants, etc.) can be configured to perform one or more of the following operations. The automated system can be configured to remove layer thickness effects if the sample wafer comprises a heterointerface material, such as, for example SOI. The layer thickness effects can be removed by using data received from a secondary analysis device, such as, for example, a spectroscopical ellipsometer (SE), a reflectometer, a CV-IV parametric analyzer, an Inductively Coupled Plasma Mass Spectrometry (ICPMS), Vapor Phase decomposition (VPD)-ICPMS, a Total Reflection X-Ray Fluorescence (TXRF), a Secondary Ion Mass Spectrometry (SIMS), a Rutherford Backscattering (RBS), a Scanning/Tunneling Electron Microscope (SEM/TEM), Atomic Force Microscope (AFM), Brightfield/Darkfield Microscopy, Glow Discharge Optical Emission Spectroscopy (GD-OES), X-Ray Photoelectron Spectroscopy ( )PS), Fourier Transform Infrared Spectroscopy (FTIR), or a microwave detected photoconductive decay (µ-PCD). The secondary analysis device can be separate from and distinct from the SHG metrology system. The system can be configured to feed the SHG signal with or without the layer thickness effects removed through a kernel (e.g., a machine learning kernel) to extract features. The extracted features can be decoded using a decoder. The decoder can be a linear or a nonlinear decoder. The decoder can be trained using supervised or unsupervised training methods. For example, in some implementations a linear decoder can be trained based on an ensemble of SHG signals together with training labels (ground truth). To train the linear decoder different models as well as different solvers can be used to efficiently solve for the different models. The different models can include, Logistic regression, L1-regularized logistic regression, Support vector machine (SVM), sparse support vector machine, Neural network and/or Deep learning. The different solvers can include Hybrid iterative shrinkage and/or Linearized Bregman approaches.

The automated system can be configured to project the decoded features from the SHG signal data (also referred to as testing data) onto a decision boundary obtained from training. The SHG signal data can be classified based on the decision. The automated system can be configured to use signal detection theory to quantify classification accuracy in terms of true positive rate vs false positive rate. In some embodiments, the automated system can be configured to use standard cross validation to access the ultimate classification accuracy Various embodiments described herein provide unique ability in isolating, controlling for, and measuring semiconductor material properties. Various embodiments described herein concern a hardware system for generating SHG signal combined with complementary techniques, as well as a suite of machine learning methods for analyzing SHG signals relative to the complementary techniques. SHG signal—including its time dependence—conveys information on a plurality of material properties including but not limited to layer thickness, trap density, local surface contamination and subsurface contamination. The subject systems enable extracting individual material parameters.

Various embodiments, together with details regarding a selection of features have been set forth above. As for other details, these may be appreciated in connection with the above-referenced patents and publications as well as is generally known or appreciated by those with skill in the art. The same may hold true with respect to method-based aspects of the disclosure in terms of additional acts as commonly or logically employed. Regarding such methods, including methods of manufacture and use, these may be carried out in any order of the events which is logically possible, as well as any recited order of events. Furthermore, where a range of values is provided, it is understood that every intervening value, between the upper and lower limit of that range and any other stated or intervening value in the stated range is encompassed. Also, it is contemplated that any optional feature of the inventive variations described may be set forth and claimed independently, or in combination with any one or more of the features described herein.

Though various embodiments have been described in reference to several examples, optionally incorporating various features, they are not to be limited to that which is described or indicated as contemplated with respect to each such variation. Changes may be made to any of the embodiments described and equivalents (whether recited herein or not included for the sake of some brevity) may be substituted without departing from the true spirit and scope hereof.

The various illustrative processes described may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, DisplayPort, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on, transmitted over or resulting analysis/calculation data output as one or more instructions, code or other information on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices.

Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Operations as described herein can be carried out on or over a website. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or HML, and via any form such as cascading style sheets ("CSS") or other.

Also, the inventors hereof intend that only those claims which use the words "means for" are to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

It is also noted that all features, elements, components, functions, acts and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and acts or steps from different embodiments, or that substitute features, elements, components, functions, and acts or steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In some instances entities are described herein as being coupled to other entities. It should be understood that the terms "interfit", "coupled" or "connected" (or any of these forms) may be used interchangeably herein and are generic to the direct coupling of two entities (without any non-negligible, e.g., parasitic, intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

Reference to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below.

It is further noted that the claims may be drafted to exclude any optional element (e.g., elements designated as such by description herein a "typical," that "can" or "may" be used, etc.). Accordingly, this statement is intended to serve as antecedent basis for use of such exclusive terminology as "solely," "only" and the like in connection with the recitation of claim elements, or other use of a "negative" claim limitation language. Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Yet, it is contemplated that any such "comprising" term in the claims may be amended to exclusive-type "consisting" language. Also, except as specifically defined herein, all technical and scientific terms used herein are to be given as broad a commonly understood meaning as possible while maintaining claim validity.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, acts, steps, or elements of the embodiments may be recited in or added to the claims, as well as negative limitations (as referenced above, or otherwise) that define the inventive scope of the claims by features, functions, steps, or elements that are not within that scope. Thus, the breadth of the variations or the inventive concepts are not to be limited to the examples provided, but only by the scope of the claim language to follow.

What is claimed is:

1. A system for characterizing a sample, comprising:
   a second harmonic generation (SHG) metrology system, the SHG metrology system comprising:
      an optical source configured to direct a beam of electromagnetic radiation to a sample; and
      an optical detector configured to detect a Second Harmonic Generation (SHG) signal from the sample, wherein the detected SHG signal includes:
         a first portion; and
         a second portion, wherein the second portion is attributed to one or more material properties of the sample; and
   a secondary analysis device separate from the SHG metrology system, the secondary analysis device configured to measure the one or more material properties of the sample; and
   an electronic processing circuit configured to:
      remove the second portion of the detected SHG signal from the detected SHG signal to obtain a parsed SHG signal data comprising the first portion of the detected SHG signal; and
      estimate a characteristic of the sample from the parsed SHG signal data.

2. The system of claim 1, wherein the secondary analysis device comprises at least one of: a reflectometer, a spectroscopic ellipsometer (SE), a CV-IV parametric analyzer, an Inductively Coupled Plasma Mass Spectrometry (ICPMS), Vapor Phase decomposition (VPD)-ICPMS, a Total Reflection X-Ray Fluorescence (TXRF), a Secondary Ion Mass Spectrometry (SIMS), a Rutherford Backscattering (RBS), a Scanning/Tunneling Electron Microscope (SEM/TEM), Atomic Force Microscope (AFM), Brightfield/Darkfield Microscopy, Glow Discharge Optical Emission Spectroscopy (GD-OES), X-Ray Photoelectron Spectroscopy (XPS), Fourier Transform Infrared Spectroscopy (FTIR), or a microwave detected photoconductive decay ($\mu$-PCD).

3. The system of claim 1, wherein the one or more material properties of the sample includes at least one of: thickness of one or more layers of the sample or presence of a known artifact.

4. The system of claim 1, wherein the characteristic of the sample estimated from the parsed SHG signal data includes one or more electrical properties of the sample.

5. The system of claim 4, wherein the one or more electrical properties of the sample includes at least one of: local surface and subsurface metal; organic or inorganic contaminants; trap charge density; strain or doping levels.

6. The system of claim 1, wherein the electronic processing circuit is configured to remove the second portion by:
   adjusting the detected SHG signal by an amount of SHG signal that is expected from a sample having the measured one or more material properties.

7. The system of claim 6, wherein adjusting the detected SHG signal comprises dividing the detected SHG signal by an amount of SHG signal that is expected from a sample having the measured one or more material properties.

8. The system of claim 1, wherein the electronic processing circuit is configured to remove the second portion by:
   deconvoluting the detected SHG signal by an amount of SHG signal that is expected from a sample having the measured one or more material properties.

* * * * *